(12) United States Patent
Apcher et al.

(10) Patent No.: US 11,110,105 B2
(45) Date of Patent: Sep. 7, 2021

(54) COMPOUNDS, COMPOSITION AND USES THEREOF FOR TREATING CANCER

(71) Applicant: INSTITUT GUSTAVE ROUSSY, Villejuif (FR)

(72) Inventors: Sébastien Apcher, Franconville (FR); Alison Pierson, Villejuif (FR); Mathilde Boulpicante, Chevilly-Larue (FR); Zafiarisoa Dolor Renko, Les Ulis (FR); Mouad Alami, Bussy Saint Georges (FR); Romain Darrigrand, Ivry sur Seine (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 16/604,599

(22) PCT Filed: Apr. 11, 2018

(86) PCT No.: PCT/EP2018/059213
§ 371 (c)(1),
(2) Date: Oct. 11, 2019

(87) PCT Pub. No.: WO2018/189210
PCT Pub. Date: Oct. 18, 2018

(65) Prior Publication Data
US 2020/0297741 A1    Sep. 24, 2020

(30) Foreign Application Priority Data

Apr. 12, 2017 (EP) .................................... 17305438
Oct. 23, 2017 (EP) .................................... 17306456

(51) Int. Cl.
| | |
|---|---|
| C07D 311/30 | (2006.01) |
| A61K 31/352 | (2006.01) |
| A61K 31/665 | (2006.01) |
| A61P 35/00 | (2006.01) |
| A61K 45/06 | (2006.01) |

(52) U.S. Cl.
CPC .......... *A61K 31/665* (2013.01); *A61K 31/352* (2013.01); *A61K 45/06* (2013.01); *A61P 35/00* (2018.01)

(58) Field of Classification Search
CPC ...... A61K 31/352; A61P 35/00; C07D 311/30
USPC .................................. 514/456; 549/220, 403
See application file for complete search history.

(56) References Cited

FOREIGN PATENT DOCUMENTS

CN      105998697      10/2016

OTHER PUBLICATIONS

Cao, Y. et al. "Bioactive flavones and biflavones from *Selaginella moefiendorffii* Hieron" *Fitoterapia*, Jun. 1, 2010, pp. 253-258, vol. 81, No. 4.
Heinhuis, B. et al. "Alternatively spliced isoforms of IL-32 differentially influence cell death pathways in cancer cell lines" *Carcinogenesis*, 2016, pp. 197-205, vol. 37, No. 2.
Yoon, S.-O. et al. "Isoginkgetin inhibits tumor cell invasion by regulating phosphatidylinositol 3-kinase/Akt-dependent matrix metalloproteinase-9 expression" *Molecular Cancer Therapeutics*, 2006, pp. Nov. 2006, pp. 2666-2675, vol. 5, No. 11.
Sui, Y. et al. "Ethyl acetate extract from *Selaginella doederleinii* Hieron inhibits the growth of human lung cancer cells A549 via caspase-dependent apoptosis pathway" *Journal of Ethnopharmacology*, Jun. 9, 2016, pp. 261-271, vol. 190.
Zhang, Y.-M. et al. "Two new flavones from the twigs and leaves of *Cephalotaxus lanceolata*" *Phytochemistry Letters*, Sep. 1, 2014, pp. 82-85, vol. 9.
Written Opinion in International Application No. PCT/EP2018/059213, dated Jun. 8, 2018, pp. 1-9.

*Primary Examiner* — Charanjit Aulakh
(74) *Attorney, Agent, or Firm* — Saliwanchik, Lloyd & Eisenschenk

(57) ABSTRACT

The present invention relates to the fields of medicine and cancer treatment. The invention more specifically relates to new compounds which are typically for use as a medicament. In particular, the invention relates to the use of these new compounds for increasing the presentation, typically the production and presentation, of Pioneer Translation Products (PTPs)-derived antigens by cancer cells in a subject, and inducing or stimulating an immune response in the subject. The present disclosure also relates to uses of such compounds, in particular to prepare a pharmaceutical composition and/or to allow or improve the efficiency of a cancer therapy in a subject in need thereof. The invention also discloses methods for preventing or treating cancer, cancer metastasis and/or cancer recurrence in a subject. The present invention in addition provides kits suitable for preparing a composition according to the present invention and/or for implementing the herein described methods.

Figure 1:
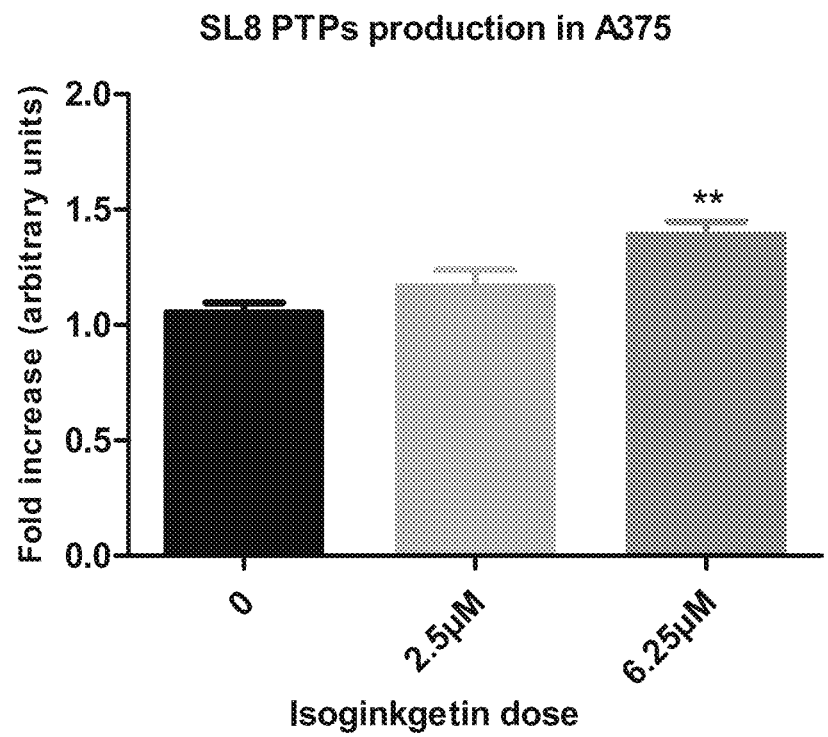
Figure 1:
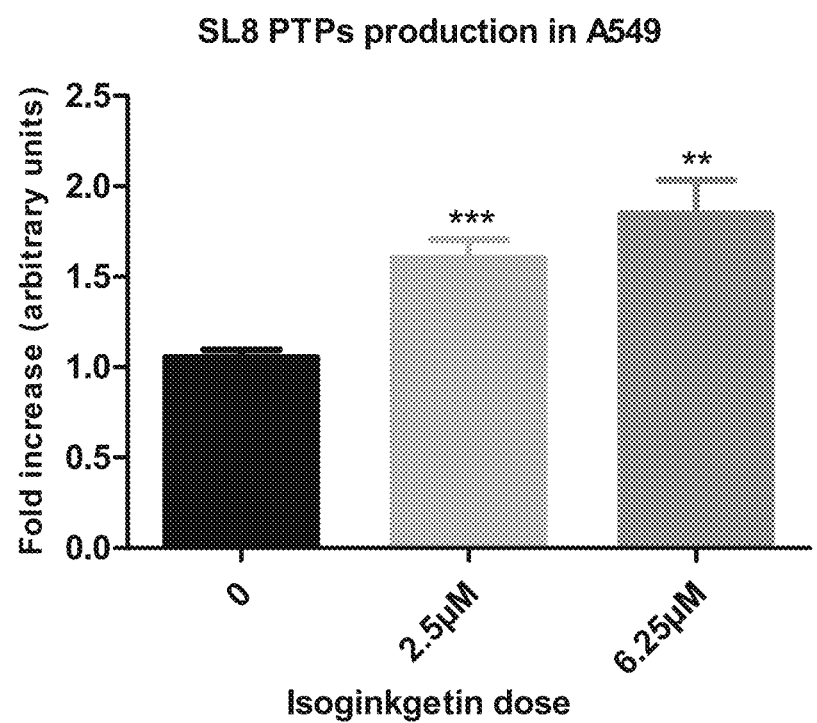
Figure 1:
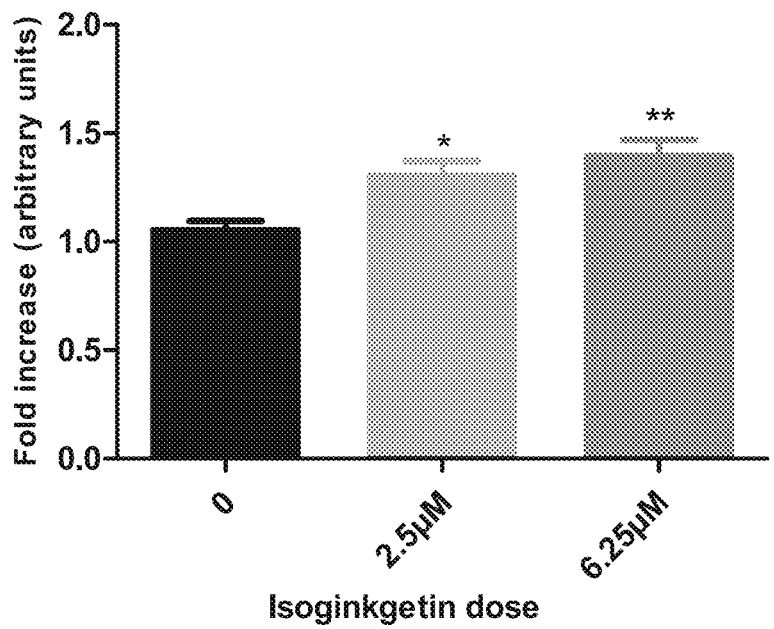
Figure 1:
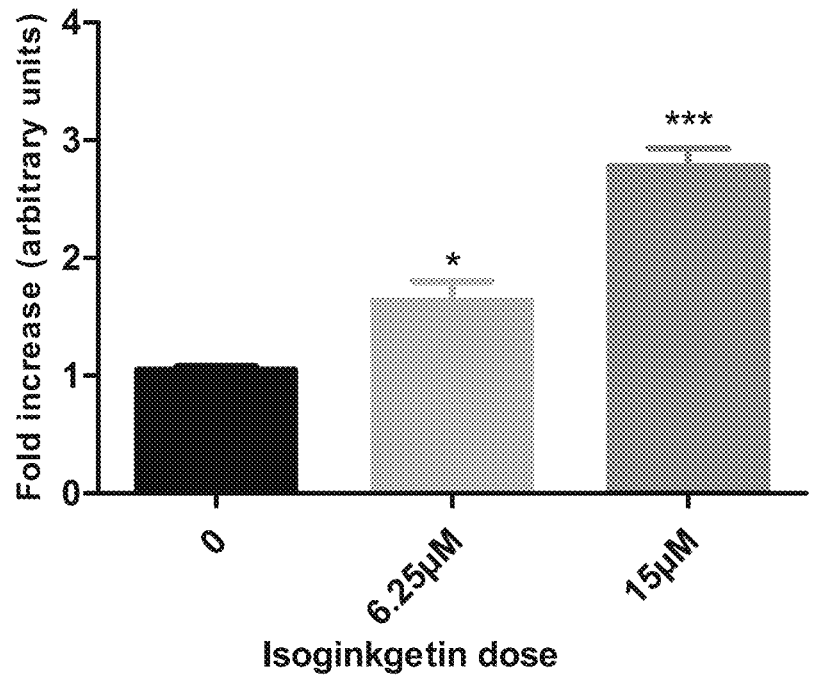
Figure 1:
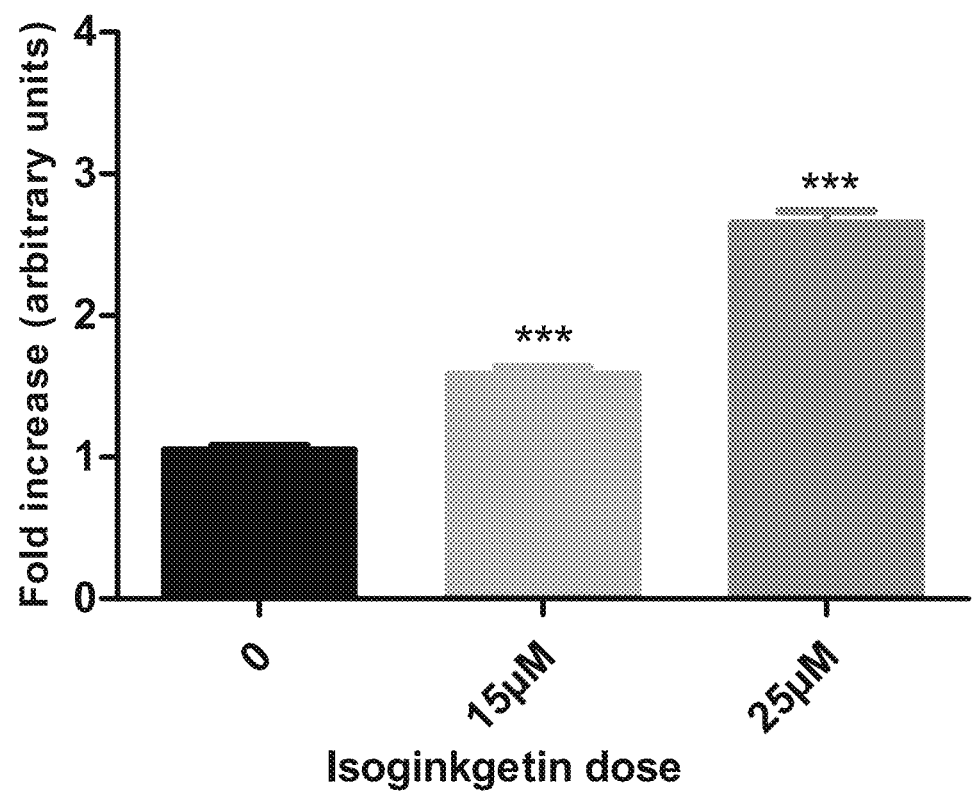

22 Claims, 25 Drawing Sheets
Specification includes a Sequence Listing.

A

B

C

D

E

A

B

C

D

E

F

A

B

A

B

C

D

E

COMPOUNDS, COMPOSITION AND USES THEREOF FOR TREATING CANCER

CROSS-REFERENCE TO RELATED APPLICATION

This application is the U.S. national stage application of International Patent Application No. PCT/EP2018/059213, filed Apr. 11, 2018.

The Sequence Listing for this application is labeled "Seq-List.txt" which was created on Oct. 1, 2019 and is 1 KB. The entire content of the sequence listing is incorporated herein by reference in its entirety.

FIELD OF THE INVENTION

The present disclosure generally relates to the fields of medicine and cancer treatment. The invention more specifically relates to new compounds which are derivatives of isoginkgetin and are each typically for use as a medicament. In particular, the invention relates to the use of these new compounds for increasing the presentation, typically the production and presentation, of (antigenic) peptides, preferably Pioneer Translation Products (PTPs)-derived antigens, by cancer cells in a subject, and inducing or stimulating an immune response in the subject. The immune response is typically directed against a tumor antigen, more generally against the cancerous tumour the subject is suffering of.

The present disclosure also relates to uses of such compounds, in particular to prepare a pharmaceutical composition and/or to allow or improve the efficiency of a cancer therapy in a subject in need thereof Each of the compounds of the invention can indeed be advantageously used, in combination with at least one distinct anticancer agent, typically a chemotherapeutic drug, and/or with radiotherapy, for treating cancer, for preventing cancer metastasis and/or for preventing cancer recurrence in a subject.

The invention also discloses methods for preventing or treating cancer, cancer metastasis and/or cancer recurrence in a subject. The present invention in addition provides kits suitable for preparing a composition according to the present invention and/or for implementing the herein described methods.

BACKGROUND OF THE INVENTION

All nucleated cells present antigenic peptides (APs) at their surface trough the class I major histocompatibility complex (MHC-I) pathway. APs are 8 to 10 amino acids long and reflect the inherent cellular activity (Caron et al.). Because their presentation guides the surveillance of potentially dangerous elements by immune cells, mainly cytotoxic CD8$^+$ T cells (CTL) and CD4$^+$ T helper cells, APs are the targets of therapeutic anti-cancer vaccines currently developed. Despite promising, clinical trials results with therapeutic vaccines targeting tumor-associated antigens (TAA) haven't met their expectations. The main failures have been associated to immunosuppressive mechanisms and to a suboptimal choice of antigens (Mellman et al.; Burg et al.). One of the important events that drive tumors immunoselection, and that is correlated to poor prognosis, is the loss or the downregulation of MHC class I antigenic presentation by tumor cells (Watson et al.; Liu et al.). These last can escape CTL and natural killer cells recognition due to defects in components of the MHC class I pathway (Leone et al.). Along with the overall decrease of MHC class I antigenic presentation, the nature of antigens presented at the cell surface, called the MHCI class I immunopeptidome (MIP), is of critical importance for immune recognition. In cancer where a specific TAA is identified and targeted with immunotherapy such as Her/neu in breast cancer or CEA in colon cancer, the loss of this TAA expression at the tumor cell surface leads to immune evasion (Lee et al.; Kmieciak et al.). To counteract that, current strategies aims at enlarging the range of targeted cancer peptide and restoring MHC antigenic presentation.

In order to understand the dynamic of the MIP, one could focus on the source of APs for the MHC class I presentation pathway. Endogenous APs were first thought to strictly come from the degradation of senescent proteins. However, models suggesting alternative sources have challenged this notion. In 1996, the group of J. Yewdell introduces the concept of the Defective ribosomal products (DRIPs) (Yewdell et al, 1996), initially described as rapidly degraded products due to their unstable conformation. More recently, inventors have explored that concept from a different perspective showing that the major source of APs derive from a pioneer translation event that occurs before introns are spliced out and that is independent of the translation event of full length proteins (Apcher et al., 2011). Produced non-canonical peptides can therefore be derived from intronic sequence, 3' or 5' UTR regions as well as alternative reading frames. These polypeptides are described as Pioneer Translation Products (PTPs). The discovery of PTPs suggests the existence of a complex translational nuclear mechanism that partly aims at shaping the MIP by generating relevant and suitable polypeptides for the MHC class I pathway. Moreover, PTPs seems to play a role in the dynamic of cancer development. When inoculated in mouse, it has been shown that cancer cells presenting PTPs-derived antigens at their surface can be recognized by specific T-cells leading to tumor growth reduction. Moreover, purified PTPs containing a model epitope efficiently promote anti-cancer immune response when injected as a peptide vaccine in mice (Duvallet et al.).

Precursor-mRNA (pre-mRNA) splicing is catalyzed in the nucleus by the spliceosome, a conserved and dynamic multi-protein complex composed of five small nuclear RNAs (snRNAs) U1, U2, U4, U5 and U6 that are complexes with over 200 proteins. A growing number of studies report that the deregulation of the spliceosome complex entails aberrant splicing patters in many cancers contributing to abnormal tumor cell proliferation and progression. Since 2011, recurrent spliceosome mutations have been reported in several cancers, including myelomonocytic leukemia, myeloid leukemia, chronic lymphocytic leukemia, breast cancers or multiple myeloma.

Inventors now herein describe new compounds for use in the treatment of cancer, in the prevention of cancer metastasis and/or in the prevention of cancer recurrence in a subject.

SUMMARY OF THE INVENTION

Inventors produced and herein describe for the first time a compound of formula

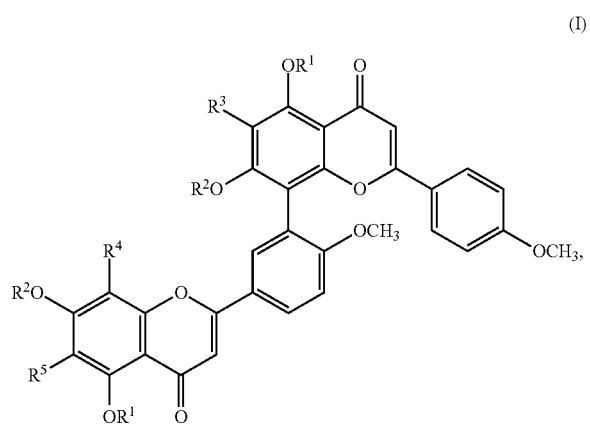

(I)

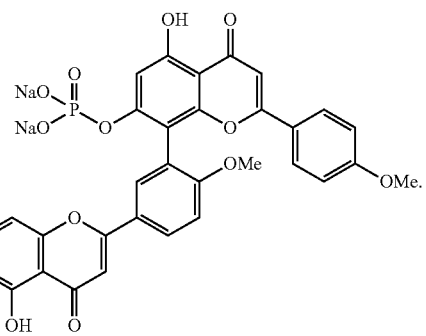

wherein $R^1$ and $R^2$ are independently selected from the group of Na, H, —$CH_3$, —$CH_2$—$CH_3$, —$CH_2$—CH=$CH_2$, n-$CH_2$—$CH_2$—$CH_3$, P(O)(O—$CH_2$—$CH_3)_2$, P(O)(OH)$_2$ or P(O)(ONa)$_2$ and wherein $R^1$, $R^2$, $R^3$, $R^4$ and $R^5$ are not H simultaneously, wherein $R^1$ is not —$CH_3$ when $R^2$ is P(O)(ONa)$_2$ or P(O)(OH)$_2$ and each of $R^3$, $R^4$ and $R^5$ is H, and wherein $R^1$ is not —$CH_3$ or H when $R^2$ is —$CH_3$ and each of $R^3$, $R^4$ and $R^5$ is H;

and wherein $R^3$, $R^4$ and $R^5$ are independently selected from the group of H, $CH_3$, —$CH_2$—$CH_3$, —$CH_2$—CH=$CH_2$, and $C_nH_{2n+1}$ with n=3–10, for use as a medicament.

This compound, as well as a stereoisomer thereof or as well as a pharmaceutically acceptable salt thereof, can advantageously be used as a medicament.

In a preferred embodiment, the invention relates to a particular compound of formula (I) wherein $R^1$ is Na, $R^2$ is P(O)(ONa)$_2$ and each of $R^3$, $R^4$ and $R^5$ is H (also herein generally identified as "IP2" or more specifically as "IP2-6Na"):

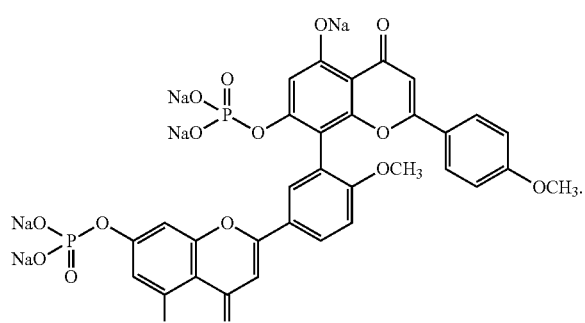

In another preferred embodiment, the invention relates to a particular compound of formula (I) wherein $R^1$ is H, $R^2$ is P(O)(ONa)$_2$ and each of $R^3$, $R^4$ and $R^5$ is H (also herein generally identified as "IP2" or more specifically as "IP2-4Na"):

In a preferred aspect herein described, the compound of formula (I), preferably a "IP2" compound (IP2-6Na or IP2-4Na), or stereoisomer or pharmaceutically acceptable salt thereof, is for use in the treatment of cancer, for use in the prevention of cancer metastasis and/or for use in the prevention of cancer recurrence in a subject.

Further described is the in vivo, in vitro or ex vivo use of a compound of formula (I), preferably a "IP2" compound (IP2-6Na or IP2-4Na), for inducing or increasing the presentation, typically the production and presentation, of (antigenic) peptides, preferably Pioneer Translation Products (PTPs)-derived antigens, by cancer cells.

The compound of formula (I), preferably a "IP2" compound (IP2-6Na or IP2-4Na), allows the physician to prevent or control, preferably decrease, cancer cell proliferation by stimulating the subject's immune system. It is in addition advantageously capable of increasing the effectiveness of other cancer treatments. Inventors herein demonstrate that this compound is in addition capable of reducing the risk of metastasis and/or cancer recurrence.

Also herein described is a composition comprising such a compound of formula (I), preferably a "IP2" compound (IP2-6Na or IP2-4Na), and a pharmaceutically acceptable carrier, preferably together with at least one distinct anticancer agent to be used simultaneously, separately or sequentially. Such a composition is typically for use for treating cancer, for preventing cancer metastasis and/or for preventing cancer recurrence in a subject.

Also herein described is a method for treating cancer in a subject, comprising a step of administering a compound, typically the compound of formula (I), preferably a "IP2" compound (IP2-6Na or IP2-4Na), or a composition as herein described to the subject.

A kit is also described which comprises the compound of formula (I), preferably a "IP2" compound (IP2-6Na or IP2-4Na), and preferably at least one distinct anticancer agent in distinct containers, as well as uses thereof, in particular to prepare a composition as herein described.

DETAILED DESCRIPTION OF THE INVENTION

Inventors generated a biflavonoid isoginkgetin derivative which is described for the first time in the context of the present invention and is identified as "compound of formula (I)":

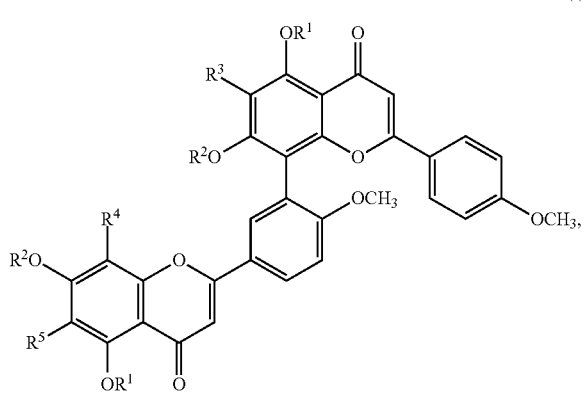

(I)

wherein $R^1$ and $R^2$ are independently selected from the group of Na, H, —CH$_3$, —CH$_2$—CH$_3$, —CH$_2$13 CH=CH$_2$, n-CH$_2$—CH$_2$—CH$_3$, P(O)(O—CH$_2$—CH$_3$)$_2$, P(O)(OH)$_2$ or P(O)(ONa)$_2$ and wherein $R^1$, $R^2$, $R^3$, $R^4$ and $R^5$ are not H simultaneously, wherein $R^1$ is not —CH$_3$ when $R^2$ is P(O)(ONa)$_2$ or P(O)(OH)$_2$ and each of $R^3$, $R^4$ and $R^5$ is H, and wherein $R^1$ is not —CH$_3$ or H when $R^2$ is —CH$_3$ and each of $R^3$, $R^4$ and $R^5$ is H;

and wherein $R^3$, $R^4$ and $R^5$ are independently selected from the group of H, CH$_3$, —CH$_2$—CH$_3$, —CH$_2$—CH=CH$_2$, and C$_n$H$_{2n+1}$ with n=3–10, preferably n=3–8.

A "hydroxymethyl" refers to a radical of formula —OMe wherein Me represents a methyl (—CH$_3$).

A "sodium hydroxide" refers to a radical of formula —ONa wherein Na represents a sodium.

The C$_n$H$_{2n+1}$ group where n=3–10 refers to an "alkyl" group which is a saturated, linear or branched aliphatic group. It includes for instance propyl, isopropyl, butyl, isobutyl, tert-butyl, pentyl, hexyl, heptyl, octyl, nonyl or decyl group. Preferably, n is from 3-8 or from 3-6.

A particular compound of formula (I) wherein $R^1$ is Na, $R^2$ is P(O)(ONa)$_2$ and each of $R^3$, $R^4$ and $R^5$ is H is also herein generally identified as "IP2" molecule or more specifically as "IP2-6Na", or as Sodium 8-(2-methoxy-5-(5-oxido-4-oxo-7-(phosphonatooxy)-4H-chromen-2-yl)phenyl)-2-(4-methoxyphenyl)-5-oxido-4-oxo-4H-chromen-7-yl phosphate:

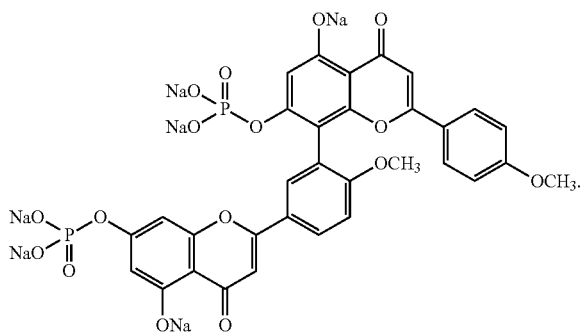

Another particular compound of formula (I) wherein $R^1$ is H, $R^2$ is P(O)(ONa)$_2$ and each of $R^3$, $R^4$ and $R^5$ is H is also herein generally identified as "IP2" molecule or more specifically as "IP2-4Na" or as sodium 5-hydroxy-8-(5-(5-hydroxy-4-oxo-7-(phosphonatooxy)-4H-chromen-2-yl)-2-methoxyphenyl)-2-(4-methoxyphenyl)-4-oxo-4H-chromen-7-yl phosphate:

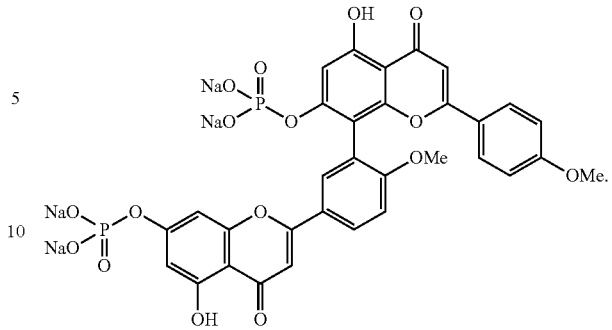

The compound of formula (I), preferably a "IP2" compound (IP2-6Na or IP2-4Na), as well as a stereoisomer thereof or a pharmaceutically acceptable salt thereof, can advantageously be used as a medicament.

As used herein, the term "pharmaceutically acceptable" refers to compositions, compounds, salts and the like that are, within the scope of sound medical judgment, suitable for contact with the tissues of the subject, or which can be administered to the subject, without excessive toxicity or other complications commensurate with a reasonable benefit/risk ratio. For instance, pharmaceutically acceptable salts encompass sodium, potassium, chloride, ammonium, acetate salts and the like.

Inventors herein demonstrate that the compound of formula (I), preferably a "IP2" compound (IP2-6Na or IP2-4Na), can advantageously be used as a positive immunomodulator against cancer.

Inventors looked at the antigenic presentation of a PTPs-derived antigen model expressed in human and mouse cancer cell lines and observed that their in vitro treatment with isoginkgetin and, more preferably IP2, increases the presentation of this antigen. In addition, they showed that in vivo treatment with the isoginkgetin dissolved in DMSO of sarcoma-bearing mice slows down tumor growth in an immune-dependent manner. In order to ameliorate its effect, they tested the isoginkgetin derivative IP2 that is soluble in water and surprisingly observed that it is a far more potent inhibitor of cancer growth than isoginkgetin itself Since in immunodeficient Nu/Nu mice, the natural product and the derivative have no effect on tumor growth they concluded that their effects are dependent on the immune response. Those results demonstrate that PTPs-derived antigenic presentation can be modulated and inventors provide a new promising molecule for market development: the IP2 splicing inhibitor or compound of formula (I) which can be used to boost the anti-cancer response and treat cancer contrary to other derivatives of isoginkgetin.

In a preferred aspect herein described, the compound of formula (I), preferably a "IP2" compound (IP2-6Na or IP2-4Na), is for use in the treatment of cancer, for use in the prevention of cancer metastasis and/or for use in the prevention of cancer recurrence in a subject.

In another preferred aspect herein described, the compound of formula (I), preferably a "IP2" compound (IP2-6Na or IP2-4Na), is for use for stimulating an anti-cancer immune response in a subject in need thereof.

In a further preferred aspect herein described, the compound of formula (I), preferably a "IP2" compound (IP2-6Na or IP2-4Na), is for use for inducing or increasing the presentation, typically the production and presentation, of Pioneer Translation Products (PTPs)-derived antigens by cancer cells.

The compound of the invention can be obtained by methods well-known by the skilled artisan such as hemisynthesis or total synthesis. An example of a method for producing the compound of formula (I) is herein described in the experimental part and further illustrated on FIG. 5 (the compound of formula (I) corresponds to compound "2" and "2") on FIG. 5, which is generally herein identified as "IP2"). The compound of formula (I) is an artificial product which cannot be found as such in nature.

The compound of formula (I) can be typically prepared from the biflavonoid Isoginkgetin which has been described as a general inhibitor of mRNA splicing and is typically extracted from leaves of maidenhair tree, Ginko biloba L. Methods for extracting Isoginkgetin are described, among others, in Kang et al (1990) and in Lee et al (1995), the disclosure of which being incorporated herein by reference.

The compound of formula (I) can also be prepared by chemical synthesis by using conventional chemical reactions.

A further object of the invention is the use of a compound of formula (I), preferably a "IP2" compound (IP2-6Na or IP2-4Na), (or a stereoisomer or a pharmaceutically acceptable salt thereof) for decreasing the resistance of a cancer or subject suffering of cancer with respect to a distinct anticancer agent, typically a distinct chemotherapeutic agent.

Also herein described is a compound of formula (I), preferably a "IP2" compound (IP2-6Na or IP2-4Na), according to the invention (or a stereoisomer or a pharmaceutically acceptable salt thereof), or a composition comprising such a compound and a pharmaceutically acceptable carrier, for use, in combination with at least one distinct anticancer agent, typically a distinct chemotherapeutic drug, and/or with radiotherapy, for treating cancer, for preventing cancer metastasis and/or for preventing cancer recurrence in a subject.

The term "subject" refers to any subject, preferably a mammal

Examples of mammals include humans and non-human animals such as, without limitation, domesticated animals (e.g., cows, sheep, cats, dogs, and horses), non-human primates (such as monkeys), rabbits, and rodents (e.g., mice and rats).The treatment is preferably intended for a human being in need thereof, whatever its age or sex.

The term "subject" typically designates a patient, in particular a patient having a tumor. Unless otherwise specified in the present disclosure, the tumor is a cancerous or malignant tumor. In a particular aspect, the subject is a subject undergoing a treatment of cancer such as chemotherapy and/or radiotherapy, or a subject at risk, or suspected to be at risk, of developing a cancer.

The subject is, for example a human being suffering of a cancer and resistant to cancer treatment, typically to chemotherapy.

The subject may have been exposed to part of a complete conventional treatment protocol, for example to at least one cycle of the all treatment protocol, for example two cycles of the all treatment protocol.

The cancer or tumor may be any kind of cancer or neoplasia. The tumor is typically a solid tumor, in particular of epithelial, neuroectodermal or mesenchymal origin. The cancer is also typically selected from a carcinoma, sarcoma, lymphoma, germ cell tumor, blastoma, leukemia and multiple myeloma, preferably from a carcinoma, sarcoma, blastoma, lymphoma, leukemia and multiple myeloma. The cancer can be a metastatic cancer or not.

The cancer can for example be selected from, without being limited to, the group consisting of chronic myeloid leukemia, acute lymphoblastic leukemia, Philadelphia chromosome positive acute lymphoblastic leukemia (Ph$^+$ ALL), Hodgkin's disease, Hodgkin's or non-Hodgkin lymphoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, brain cancer, central nervous system cancer, pancreatic cancer, glioblastoma multiforme, cervical cancer, stomach cancer, bladder cancer, malignant hepatoma, breast cancer, colon carcinoma, head and neck cancer, gastric cancer, germ cell tumor, pediatric sarcoma, rhabdomyosarcoma, Ewing's sarcoma, osteosarcoma, soft tissue sarcoma, sinonasal NK/T-cell lymphoma, myeloma, melanoma, multiple myeloma, acute myelogenous leukemia (AML), and chronic lymphocytic leukemia.

In a preferred embodiment, the cancer is selected from the group consisting of lung cancer, breast cancer, genitourinary cancer (such as prostate cancer, bladder cancer, testis cancer, uterine cervix cancer or ovaries cancer) and sarcoma (such as osteosarcoma or soft tissue sarcoma, including pediatric soft tissue sarcoma, neuroblastoma, myeloma and melanoma).

More preferably, the cancer is selected from melanoma, lung cancer (including non-small-cell lung carcinoma (or NSCLC) and small-cell lung carcinoma (or SCLC)) and breast cancer.

Even more preferably, the carcinoma is a melanoma or a lung cancer.

In an aspect, the cancer is a lung cancer, typically a small-cell lung cancer or a non-small cell lung cancer.

In another aspect, the cancer is a leukemia, typically an acute myelogenous leukemia (AML) or a chronic lymphocytic leukemia.

In a further aspect, the cancer is a colon cancer, typically a colon carcinoma. The cancer may also be a colorectal cancer.

In a further aspect, the cancer is a pediatric cancer typically a pediatric sarcoma, lymphoma, leukemia, neuroblastoma, brain cancer, or central nervous system cancer.

In a particular aspect herein described, the anticancer agent is selected from a chemotherapeutic agent, an immune checkpoint blocker and an anti-cancer vaccine (also herein identified as "cancer vaccine"). These agents are typically considered as "conventional" agents for treating cancer.

The chemotherapeutic agent is typically an agent selected for example from an antitumor/cytotoxic antibiotic, an alkylating agent, an antimetabolite, a topoisomerase inhibitor, a mitotic inhibitor, a platin based component, a specific kinase inhibitor, an hormone, a cytokine, an antiangiogenic agent, an antibody, a DNA methyltransferase inhibitor and a vascular disrupting agent.

The antitumor agent or cytotoxic antibiotic can for example be selected from an anthracycline (e.g. doxorubicin, daunorubicin, adriamycine, idarubicin, epirubicin, mitoxantrone, valrubicin), actinomycin, bleomycin, mitomycin C, plicamycin and hydroxyurea.

The alkylating agent can for example be selected from mechlorethamine, cyclophosphamide, melphalan, chlorambucil, ifosfamide, temozolomide busulfan, N-Nitroso-N-methylurea (MNU), carmustine (BCNU), lomustine (CCNU), semustine (MeCCNU), fotemustine, streptozotocin, dacarbazine, mitozolomide, thiotepa, mytomycin, diaziquone (AZQ), procarbazine, hexamethylmelamine and uramustine.

The antimetabolite can for example be selected from a pyrimidine analogue (e.g. a fluoropyrimidine analog, 5-fluorouracil (5-FU), floxuridine (FUDR), cytosine arabinoside (Cytarabine), Gemcitabine (Gemzar®), capecitabine); a purine analogue (e.g. azathioprine, mercaptopurine, thioguanine, fludarabine, pentostatin, cladribine, clofarabine); a folic acid analogue (e.g. methotrexate, folic acid, pemetrexed, aminopterin, raltitrexed, trimethoprim, pyrimethamine).

The topoisomerase inhibitor can for example be selected from camptothecin, irinotecan, topotecan, amsacrine, etoposide, etoposide phosphate and teniposide.

The mitotic inhibitor can for example be selected from a taxane [paclitaxel (PG-paclitaxel and DHA-paclitaxel) (Taxol®), docetaxel (Taxotère®), larotaxel, cabazitaxel, ortataxel, tesetaxel, or taxoprexin]; a spindle poison or a vinca alkaloid (e.g. vincristine, vinblastine, vinorelbine, vindesine or vinflunine); mebendazole; and colchicine.

The platin based component can for example be selected from platinum, cisplatin, carboplatin, nedaplatin, oxaliplatin, satraplatin and triplatin tetranitrate.

The specific kinase inhibitor can for example be selected from a BRAF kinase inhibitor such as vemurafenib; a MAPK inhibitor (such as dabrafenib); a MEK inhibitor (such as trametinib); and a tyrosine kinase inhibitor such as imatinib, gefitinib, erlotinib, sunitinib or carbozantinib.

Tamoxifen, an anti-aromatase, or an anti-estrogen drug can also typically be used in the context of hormonotherapy.

A cytokine usable in the context of an immunotherapy can be selected for example from IL-2 (Interleukine-2), IL-11 (Interleukine-11), IFN (Interferon) alpha (IFNa), and Granulocyte-macrophage colony-stimulating factor (GM-CSF).

The anti-angiogenic agent can be selected for example from bevacizumab, sorafenib, sunitinib, pazopanib and everolimus.

The antibody, in particular the monoclonal antibody (mAb) can be selected from an anti-CD20 antibody (anti-pan B-Cell antigen), anti-Her2/Neu (Human Epidermal Growth Factor Receptor-2/NEU) antibody; an antibody targeting cancer cell surface (such as rituximab and alemtuzumab); an antibody targeting growth factor (such as bevacizumab, cetuximab, panitumumab and trastuzumab); an agonistic antibody (such as anti-ICOS mAb, anti-OX40 mAb, anti-41BB mAb); and an immunoconjugate (such as 90Y-ibritumomab tiuxetan, 131I-tositumomab, or ado-trastuzumab emtansine).

A DNA methyltransferase inhibitor can for example be selected from 2'-deoxy-5-azacytidine (DAC), 5-azacytidine, 5-aza-2'-deoxycytidine, 1-[beta]-D-arabinofuranosyl-5-azacytosine and dihydro-5-azacytidine.

A vascular disrupting agent can for example be selected from a flavone acetic acid derivative, 5,6-dimethylxanthenone-4-acetic acid (DMXAA) and flavone acetic acid (FAA).

Other chemotherapeutic drugs include a proteasome inhibitor (such as bortezomib), a DNA strand break compound (such as tirapazamine), an inhibitor of both thioredoxin reductase and ribonucleotide reductase (such as xcytrin), and an enhancer of the Th1 immune response (such as thymalfasin).

In a preferred embodiment, the chemotherapeutic drug or agent is selected from an antitumor/cytotoxic antibiotic, an alkylating agent, an antimetabolite, a topoisomerase inhibitor, a mitotic inhibitor, a platin based component, a specific kinase inhibitor, an antiangiogenic agent, an antibody and a DNA methyltransferase inhibitor.

An immune checkpoint blocker is typically an antibody targeting an immune checkpoint. Such an immune checkpoint blocker can be advantageously selected from anti-CTLA4 (ipilimumab and Tremelimumab), anti-PD-1 (Nivolumab and Pembrolizumab), anti-PD-L1 (Atezolizumab, Durvalumab, and Avelumab), anti-PD-L2 and anti-Tim3.

The cancer vaccine can for example be selected from a vaccine composition comprising (antigenic) peptides, in particular PTPs; a Human papillomavirus (HPV) vaccine (such as Gardasil®, Gardasil9®, and Cervarix®); a vaccine stimulating an immune response to prostatic acid phosphatase (PAP) sipuleucel-T (Provenge®); an oncolytic virus; and talimogene laherparepvec (T-VEC or Imlygic®).

In another particular aspect, the ("conventional") cancer treatment is an irradiation (also herein identified as "radiotherapy"). The radiotherapy typically involves rays selected from X-rays ("XR"), gamma rays and/or UVC rays.

The treatment which can include several anticancer agents is selected by the cancerologist depending on the specific cancer to be prevented or treated.

A particular melanoma is a melanoma conventionally treated with ipilimumab, nivolumab, pembrolizumab, IFNa, dacarbazine, a BRAF inhibitor, dabrafenib, trametinib, sorafenib, temozolomide, electrochemotherapy, TNFalpha and/or fotemustine.

In a particular embodiment, the melanoma is a melanoma resistant to the previously described cytotoxic conventional therapies.

A particular breast cancer is a breast cancer conventionally treated with an anthracycline, a taxane, trastuzumab, an anti-PARP (Poly (ADP-ribose) polymerase), an anti-PI3K (Phosphoinositide 3-kinase), a mTOR (mammalian Target of Rapamycin) inhibitor, vinorelbine, gemcitabine, an antioestrogen, and/or an antiaromatase, before or after a surgical step to remove breast tumor, preferably before such a surgical step.

In a particular embodiment, the breast cancer is a breast cancer resistant to the previously described conventional therapies.

A particular lung cancer is a lung cancer conventionally treated with XR and either platine or permetrexed.

A particular early stage NSCLC is an NSCLC conventionally treated with paclitaxel, docetaxel gemcitabine, vinorelbine, etoposide, taxane, avastin [anti-VEGF (Vascular endothelial growth factor) antibody], erlotinib and/or gefitinib. In a particular embodiment, the lung cancer is resistant to conventional therapies.

The present disclosure further relates to the use of the compound of formula (I) of the invention, preferably "IP2", to prepare a pharmaceutical composition or medicament, said composition being capable of treating cancer or of improving the efficiency of a therapy of cancer in a subject in need thereof by stimulating the subject's immune system. The compound of the invention can in particular be advantageously used, in combination with at least one distinct anti-cancer agent as described previously or any other therapeutically active compound, and/or with radiotherapy, for treating cancer, for preventing cancer metastasis and/or for preventing cancer recurrence in a subject.

Also herein described is thus a composition comprising, typically as a combined preparation, a compound of formula (I), preferably a "IP2" compound (IP2-6Na or IP2-4Na), and a pharmaceutically acceptable carrier, preferably together with at least one distinct anticancer agent, for simultaneous, separate or sequential use in the treatment of said cancer.

Herein described are also (i) a method for preventing or treating cancer, (ii) a method for increasing the sensitivity of a cancer to an anticancer agent, and (iii) a method for decreasing the resistance of a cancer with respect to an anticancer agent, each of said methods comprising administering a subject in need thereof with an effective amount, typically a therapeutically effective amount, of at least one compound of formula (I), preferably a "IP2" compound (IP2-6Na or IP2-4Na), or a pharmaceutical composition as defined above, preferably together with an anticancer agent classically used in the prevention or treatment of cancer as herein described (as a combined preparation).

In another particular aspect, said method further comprises administering an effective amount of another therapeutically active compound for preventing or treating cancer or a cancer treatment side effect.

As used herein, "treatment" or "treat" refers to therapeutic intervention in an attempt to alter the natural course of the subject being treated, and can be performed either for preventive (prophylactic) or curative purpose. Desirable effects of treatment include, but are not limited to, preventing occurrence or recurrence of disease, alleviation of symptoms, and diminishment of any direct or indirect pathological consequences of the disease, decreasing the rate of disease progression, amelioration or palliation of the disease state, and remission or improved prognosis. In preferred embodiments, compositions and methods of the invention are used to delay development of a cancer or to slow the progression of a cancer, typically of tumor growth.

Typically, the treatment will induce a therapeutic response of the immune system of the subject, typically $CD4^+$ and/or $CD8^+$ T cells response(s).

By inducing a T cell response is typically meant herein that a T cell response directed towards a certain antigen is elicited. Before said induction, said T cell response was not present, or below detection levels or not functional. By enhancing a T cell response is meant herein that the overall action of T cells directed towards a certain antigen is made higher and/or more efficient compared to the overall action of said T cells before said enhancement. For instance, after said enhancement more T cells directed towards said antigen may be generated. As a result, the action of the additionally generated T cells increases the overall action against said antigen. Alternatively, said enhancement may comprise the increment of the action of T cells directed towards said antigen. Said T cells may for instance react stronger and/or quicker with said antigen. Of course, the result of said enhancement may be generation of additional T cells together with increment of the action of said T cells. Alternatively, said enhancement may comprise generation of additional T cells, or increment of the action of T cells, only.

Another object herein described relates to a method of producing an immune response in a subject, typically against a specific target, preferably a tumor antigen or cancer/tumor cell or tissue, the method comprising injecting to said subject a compound of formula (I) according to the invention or composition according to the invention comprising such a compound, typically in an effective amount. The detection of a therapeutic immune response can be easily determined by the skilled person thanks to technologies such as ELISA, ELISPOT, delayed type hypersensitivity response, intracellular cytokine staining, and/or extracellular cytokine staining.

As used herein, "an effective amount or dose" or "a therapeutically effective amount or dose" refers to an amount of the compound of the invention which prevents, removes, slows down the cancer or reduces or delays one or several symptoms or disorders caused by or associated with said disease in the subject, or which induce a measurable immune response in the subject, who is preferably a human being. The effective amount, and more generally the dosage regimen, of the compound of the invention and pharmaceutical compositions thereof may be determined and adapted by the one skilled in the art. An effective dose can be determined by the use of conventional techniques and by observing results obtained under analogous circumstances. The therapeutically effective dose of the compound of the invention will vary depending on the disease to be treated or prevented, its gravity, the route of administration, any co-therapy involved, the patient's age, weight, general medical condition, medical history, etc.

Typically, the amount of the compound to be administrated to a patient may range from about 0.01 mg/kg to 500 mg/kg of body weight for a human patient. In a particular embodiment, the pharmaceutical composition according to the invention comprises 0.1 mg/kg to 100 mg/kg of the compound of the invention, for instance from 0.5 mg/kg to 10 mg/kg.

In a particular aspect, the compounds of the invention can be administered to the subject by parenteral route, oral route, or intraveinous (IV), intratumoral (IT) or intraperitoneal (IP) injection. The compound or the nanoparticle of the invention may be administered to the subject daily (1time a day) during several consecutive days, for example during 2 to 10 consecutive days, preferably from 3 to 6 consecutive days. Said treatment may be repeated during 1, 2, 3, 4, 5, 6 or 7 weeks, or every two or three weeks or every one, two or three months. Alternatively, several treatment cycles can be performed, optionally with a break period between two treatment cycles, for instance of 1, 2, 3, 4 or 5 weeks. The compound of the invention can for example be administered as a single dose once a week, once every two weeks, or once a month. The treatment may be repeated one or several times per year. Doses are administered at appropriate intervals which can be determined by the skilled person. The amount chosen will depend on multiple factors, including the route of administration, duration of administration, time of administration, the elimination rate of the selected compound of formula (I), or of the various products used in combination with said compound, the age, weight and physical condition of the patient and his/her medical history, and any other information known in medicine.

The administration route can be performed by various routes. For example it can be oral or parenteral. It is typically performed by systemic injection, e.g., intravenous, intra-muscular, intra-peritoneal, intra-tumoral, sub-cutaneous, etc. The pharmaceutical composition is adapted for one or several of the above-mentioned routes. The pharmaceutical composition is preferably administered by injection or by intravenous infusion of suitable sterile solutions, or in the form of liquid or solid doses via the alimentary canal.

The pharmaceutical composition can be formulated as solutions in pharmaceutically compatible solvents or vehicles, or as pills, tablets, capsules, powders, suppositories, etc. that contain solid vehicles in a way known in the art, possibly through dosage forms or devices providing sustained and/or delayed release. For this type of formulation, an agent such as cellulose, lipids, carbonates or starches are used advantageously.

Agents or vehicles that can be used in the formulations (liquid and/or injectable and/or solid) are excipients or inert vehicles, i.e. pharmaceutically inactive and non-toxic vehicles.

Mention may be made, for example, of saline, physiological, isotonic and/or buffered solutions, compatible with pharmaceutical use and known to those skilled in the art. The compositions may contain one or more agents or vehicles chosen from dispersants, solubilizers, stabilizers, preservatives, etc.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations suitable for parenteral administration conveniently comprise a sterile oily or aqueous preparation of the active ingredient which is preferably isotonic with the blood of the recipient. Every such formulation can also contain other pharmaceutically compatible and non-toxic auxiliary agents, such as, e.g. stabilizers, antioxidants, binders, dyes, emulsifiers or flavouring substances.

The formulations of the present invention comprise an active ingredient, the compound of formula (I), preferably "IP2", in association with a pharmaceutically acceptable carrier and optionally with other active or therapeutic ingredients. The carrier must be "acceptable" in the sense of being compatible with the other ingredients of the formulations and not deleterious to the recipient thereof Methods for the safe and effective administration of most of these anti-cancer agents are known to those skilled in the art. In addition, their administration is described in the standard literature.

Another object of the invention is a kit comprising at least one compound of formula (I) according to the invention, preferably "IP2", and preferably at least one distinct anti-cancer agent, typically chemotherapeutic drug, in distinct containers. The kit can further comprise instructions for preparing a composition according to the invention, for carrying out anyone of the herein described method, for example for preventing or treating cancer, for preventing or treating cancer metastasis and/or for preventing or treating cancer recurrence in a subject.

In a particular embodiment, the present invention relates to the use of a kit according to the invention to prepare a composition as herein described.

In another particular embodiment, the kit is suitable for implementing anyone of the herein described method, in particular a method for treating cancer, for preventing cancer metastasis and/or for preventing cancer recurrence in a subject.

Further aspects and advantages of the present invention will be disclosed in the following experimental section and figures which shall be considered as illustrative only.

LEGENDS TO THE FIGURES

FIG. 1: Isoginkgetin treatment increases antigenic presentation of intron-derived antigens in cancer cells.

B3Z specific T-cell activation after treatment with 2,5 μM and 6,25 μM isoginkgetin of (A) human melanoma cell line A375, (B) human lung carcinoma cell line A549, (C) normal lung fibroblast cell line MRC5. (D) B3Z specific T-cell activation after treatment with 6,25 μM and 15 μM isoginkgetin of mouse melanoma cell line B16F10. (E) B3Z specific T-cell activation after treatment with 15 μM and 25 μM isoginkgetin of mouse sarcoma cell line MCA205.

Figure 2:
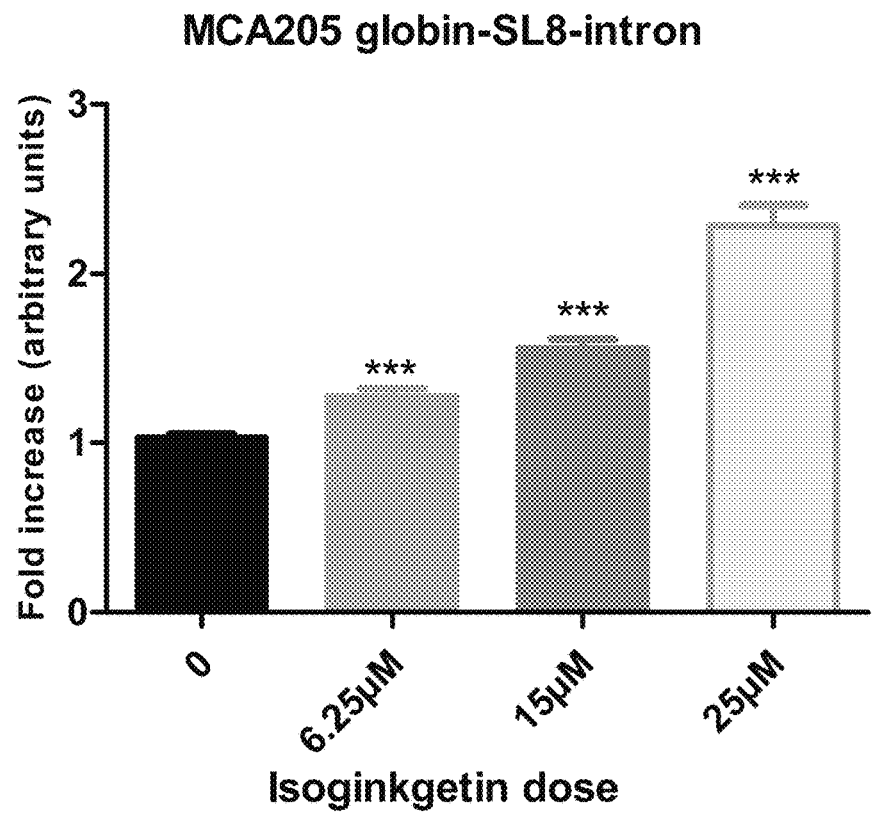
Figure 2:
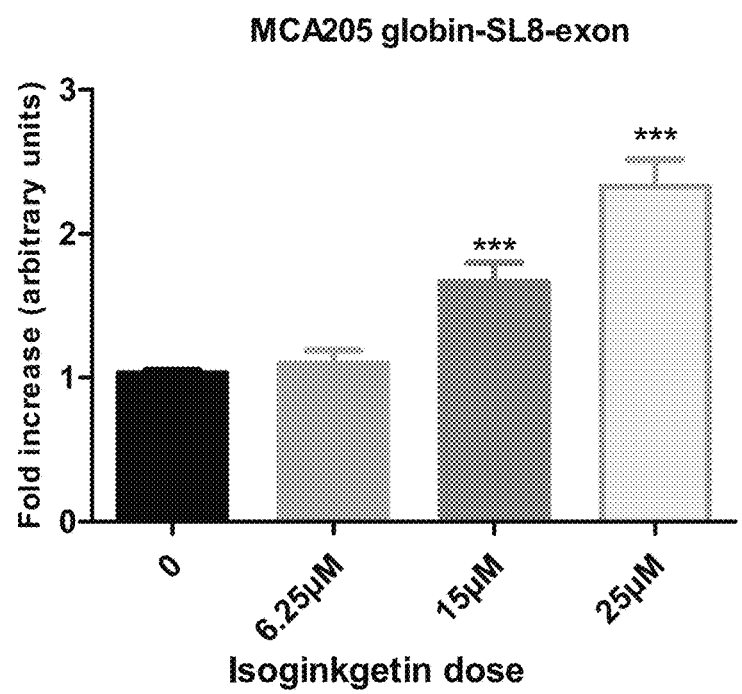
Figure 2:
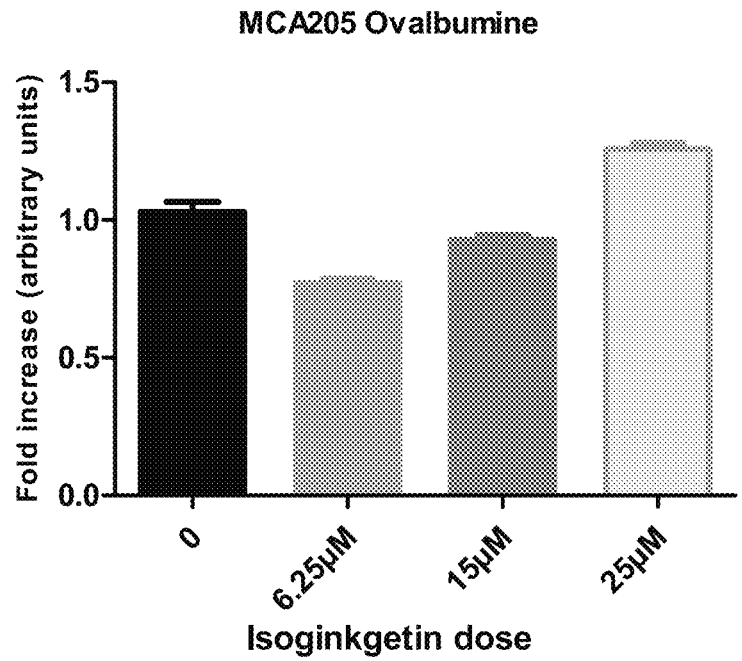
Figure 2:
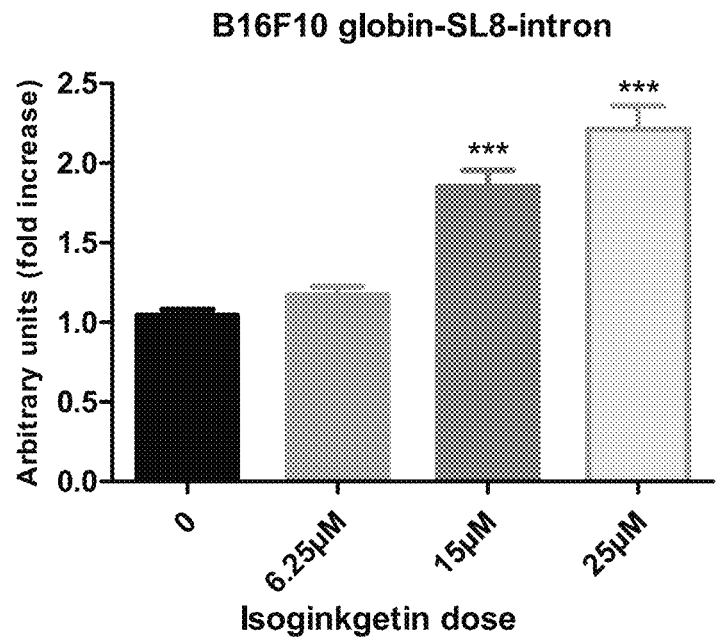
Figure 2:
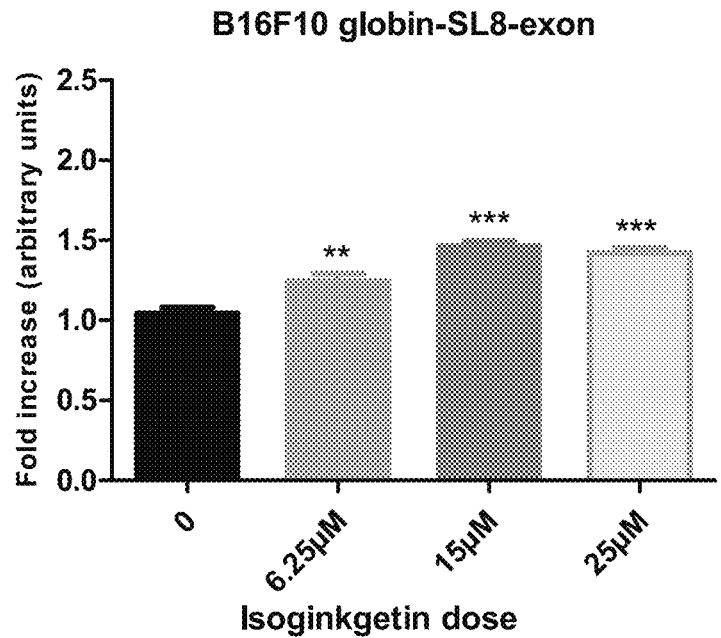
Figure 2:
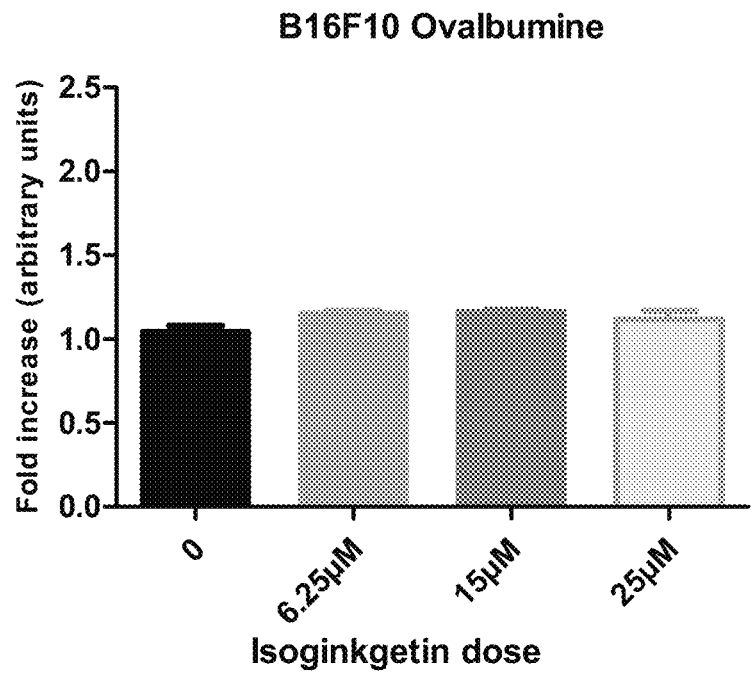

FIG. 2: Isoginkgetin treatment increases antigenic presentation of intron-derived antigens in cancer cells.

B3Z specific T-cell activation after treatment with 6,25 μM, 15 μM and 25 μM isoginkgetin of MCA205 cells previously transfected with (A) globin-SL8-intron construct, (B) globin-SL8-exon construct, (C) Ovalbumin construct.

B3Z specific T-cell activation after treatment with 6,25 μM, 15 μM and 25 μM isoginkgetin of B16F10 cells previously transfected with (D) globin-SL8-intron construct, (E) globin-SL8-exon construct, (F) Ovalbumin construct. Data are given as mean ±SEM. *P<0.05, P<0.01, *P<0.001 (unpaired student t test).

Figure 3:
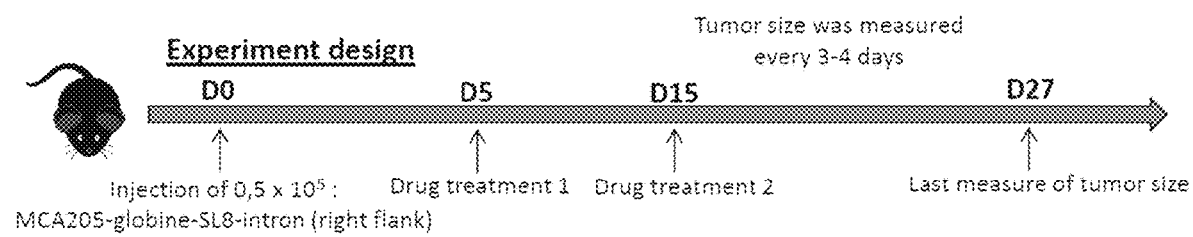
Figure 3:
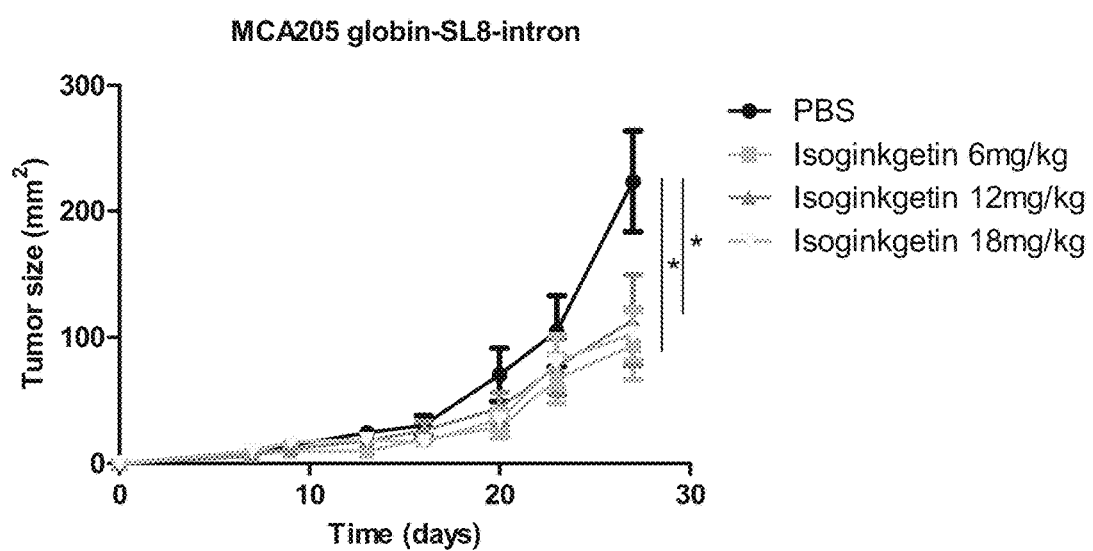

FIG. 3: Isoginkgetin treatment slows clown tumor growth in vivo.

(A) Experimental settings. (B) MCA205 globin-SL8-intron cells were inoculated subcutaneously on the mice flank. Five days and fifteen days later, 6 mg/kg, 12 mg/kg or 18 mg/kg isoginkgetin was injected intraperitoneally. Tumor size was assessed every 3 to 4 days until day 27. Each line represents the tumor size in area (mm$^2$) of 6 mice in each group. Data are given as mean ±SEM. *p<0.05 (ANOVA with Tukey's multiple comparison test comparing all groups).

Figure 4:
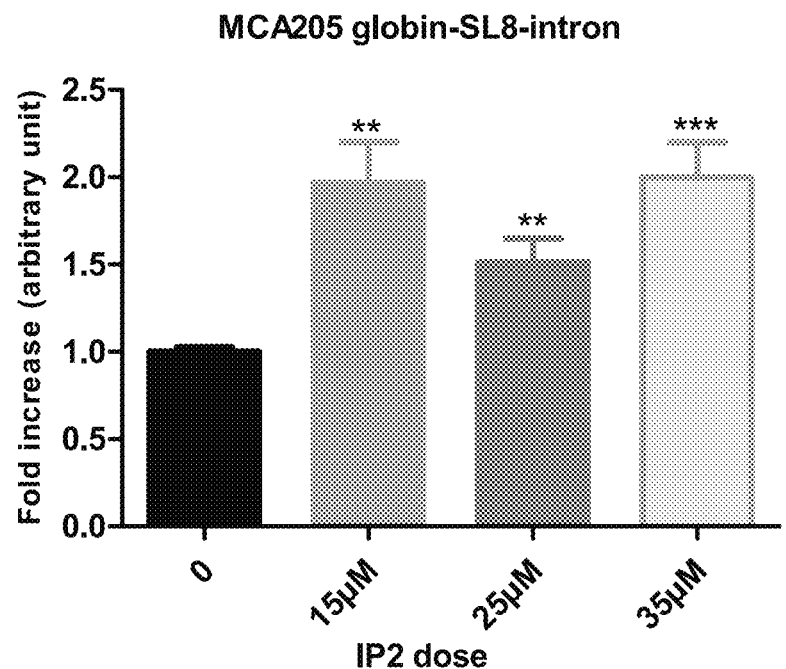
Figure 4:
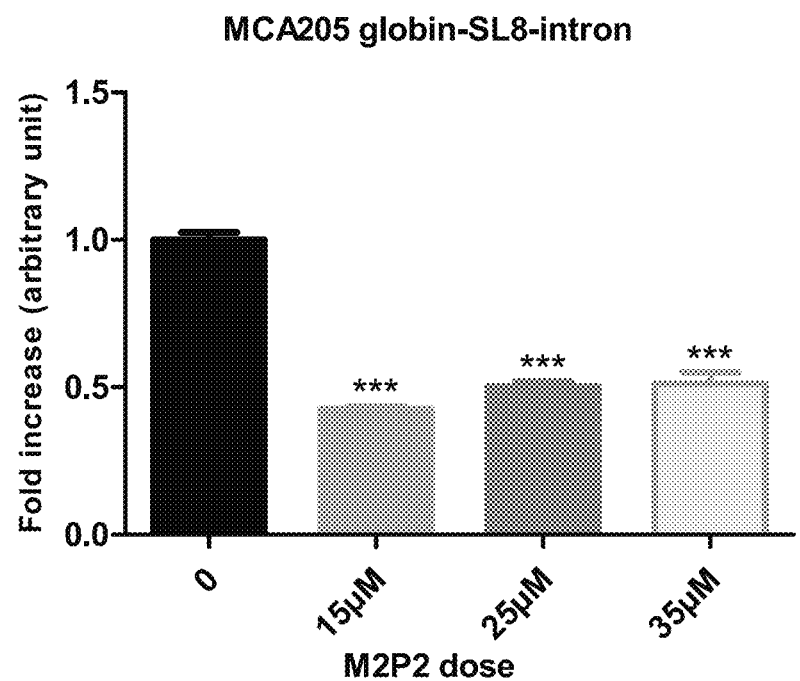
Figure 4:
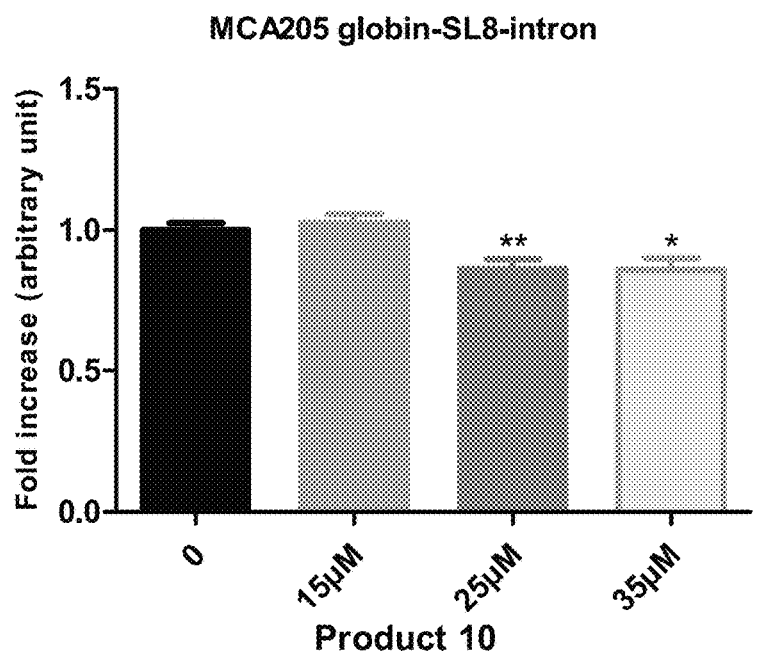
Figure 4:
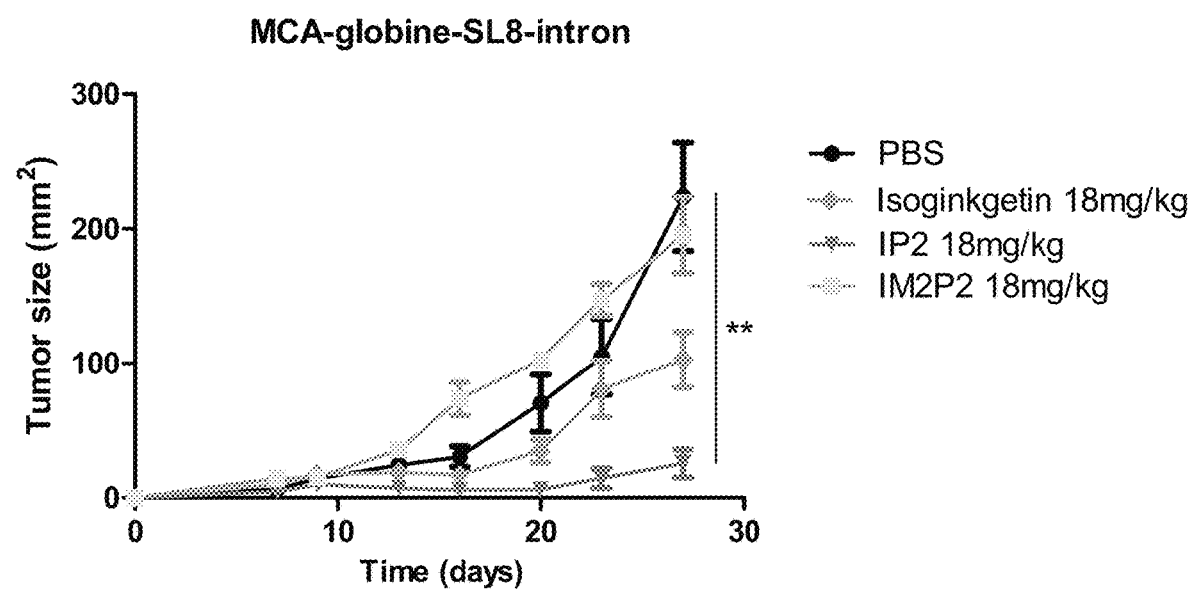
Figure 4:
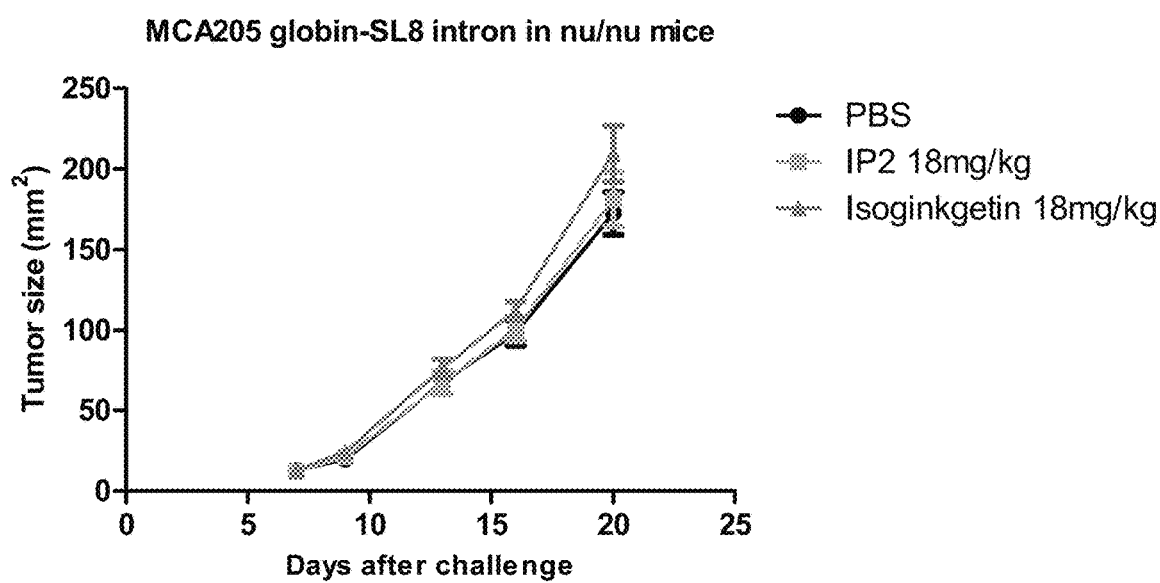

FIG. 4: Isoginkgetin derivative IP2 efficiently increases MHC class I presentation of intron-derived antigen in vitro and reduces tumor growth in vivo in an immune-dependent manner.

B3Z specific T-cell activation after treatment of MCA205 cells expressing intron-derived SL8 antigen with 15 μM, 25 μM and 35 μM (A) IP2 or (B) IM2P2, (C) product 10. (D) MCA205 globin-SL8-intron cells were inoculated subcutaneously on the C56BL/7 mice flank. Five days and fifteen days later, PBS or 18 mg/kg of isoginkgetin, IP2, or M2P2 was injected intraperitoneally. Tumor size was assessed every 3 to 4 days until day 27. Each line represents the tumor size in area (mm$^2$) of 6 mice in each group. Data are given as mean ±SEM. *p<0.05, **p<0.01 (ANOVA with Tukey's multiple comparison test comparing all groups). (E) MCA205 globin-SL8-intron cells were inoculated subcutaneously on the Nude nu/nu mice flank. Five days and fifteen days later, PBS, 18 mg/kg of isoginkgetin or IP2 was injected intraperitoneally. Tumor size was assessed every 3 to 4 days until day 27. Each line represents the tumor size in area (mm$^2$) of 6 mice in each group. Data are given as mean ±SEM.

Figure 5:
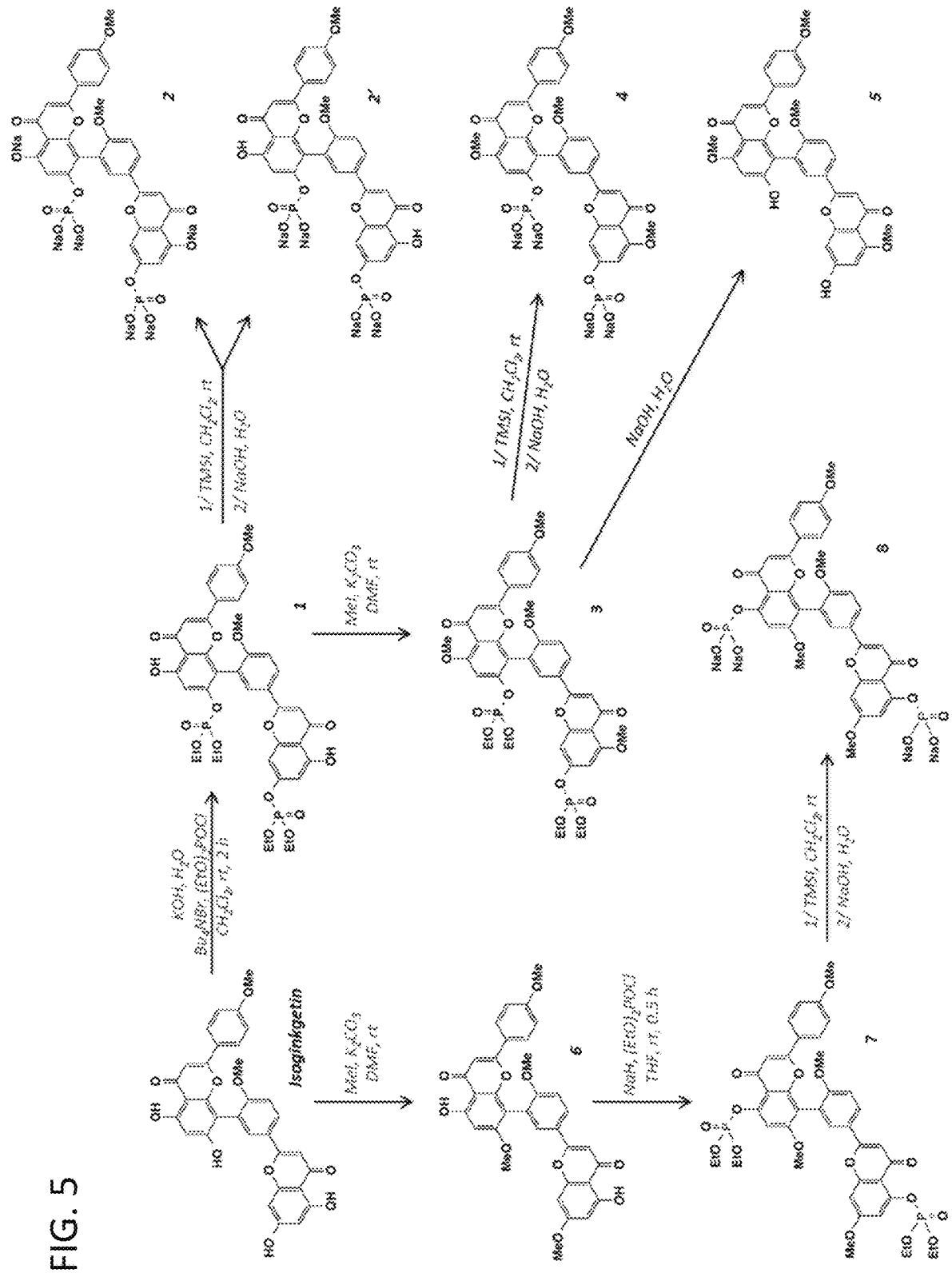

FIG. 5: Schema of synthesis of isoginkgetin derivatives.

Figure 6:
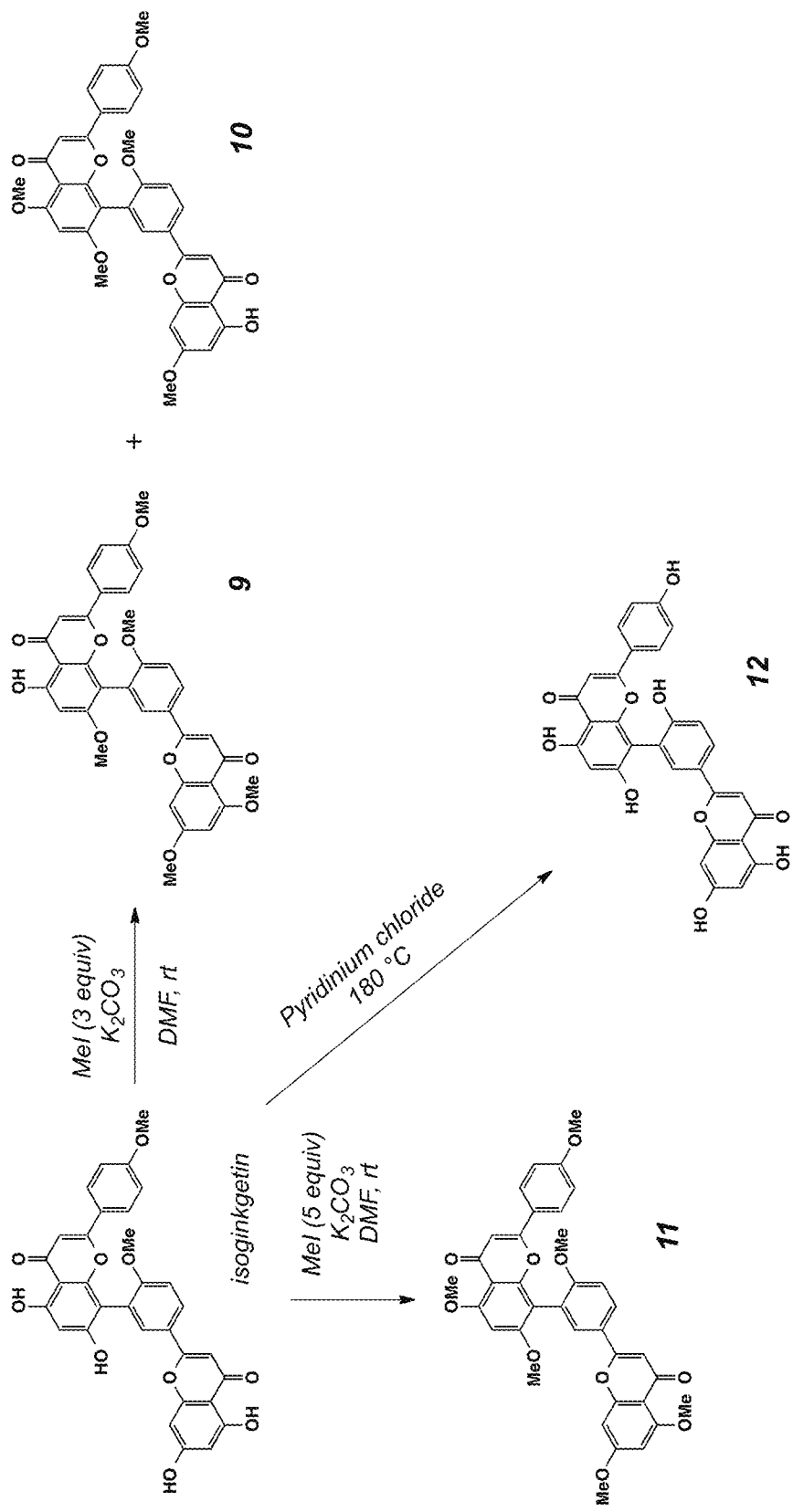

FIG. 6: Schema of synthesis of isoginkgetin derivatives.

Figure 7:
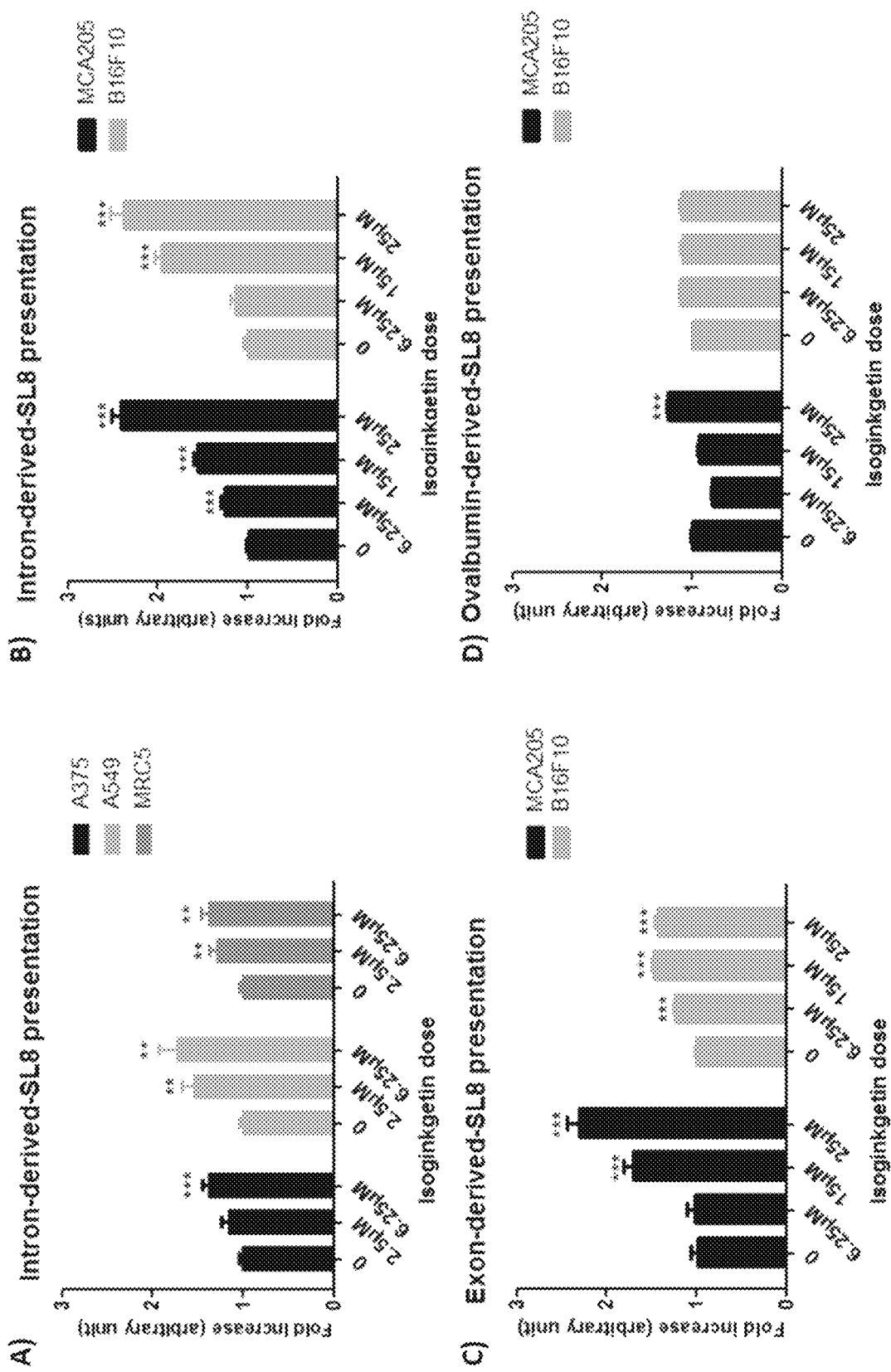

FIG. 7: Splicing inhibition increases exon- and intron-derived antigens MHC-I presentation in cancer cells.

B3Z SL8-specific T-cell activation after co-culture with (A) human melanoma A375, human lung carcinoma A549 or normal human lung fibroblast MRC5 cell lines, all transiently expressing the intron-derived SL8 peptide and the H2-K$^b$ molecules and treated upstream with 2,5 μM or 6,25 μM isoginkgetin for 18 hours; or with (B) mouse sarcoma MCA205 or mouse melanoma B16F10 cell lines both transiently expressing the intron-derived SL8 peptide and treated upstream with 6,25 μM, 15 μM or 25 μM isoginkgetin for 18 hours. B3Z activation after co-culture with MCA205 or B16F10 cells that both transiently express (C) the exon-derived SL8 peptides or (D) the Ova cDNA construct, which doesn't need to be spliced, treated upstream with 6,25 μM, 15 μM or 25 μM isoginkgetin for 18 hours. Free SL8 peptides were added in each condition to ensure that T-cell assays were carried out at non-saturated conditions and that the expression of MHC-I molecules was taking into account in the results. Each graph is one representative of at least four independent experiments.

Data are given as mean ±SEM. *P<0.05, P<0.01, *P<0.001 (unpaired student t test).

Figure 8:
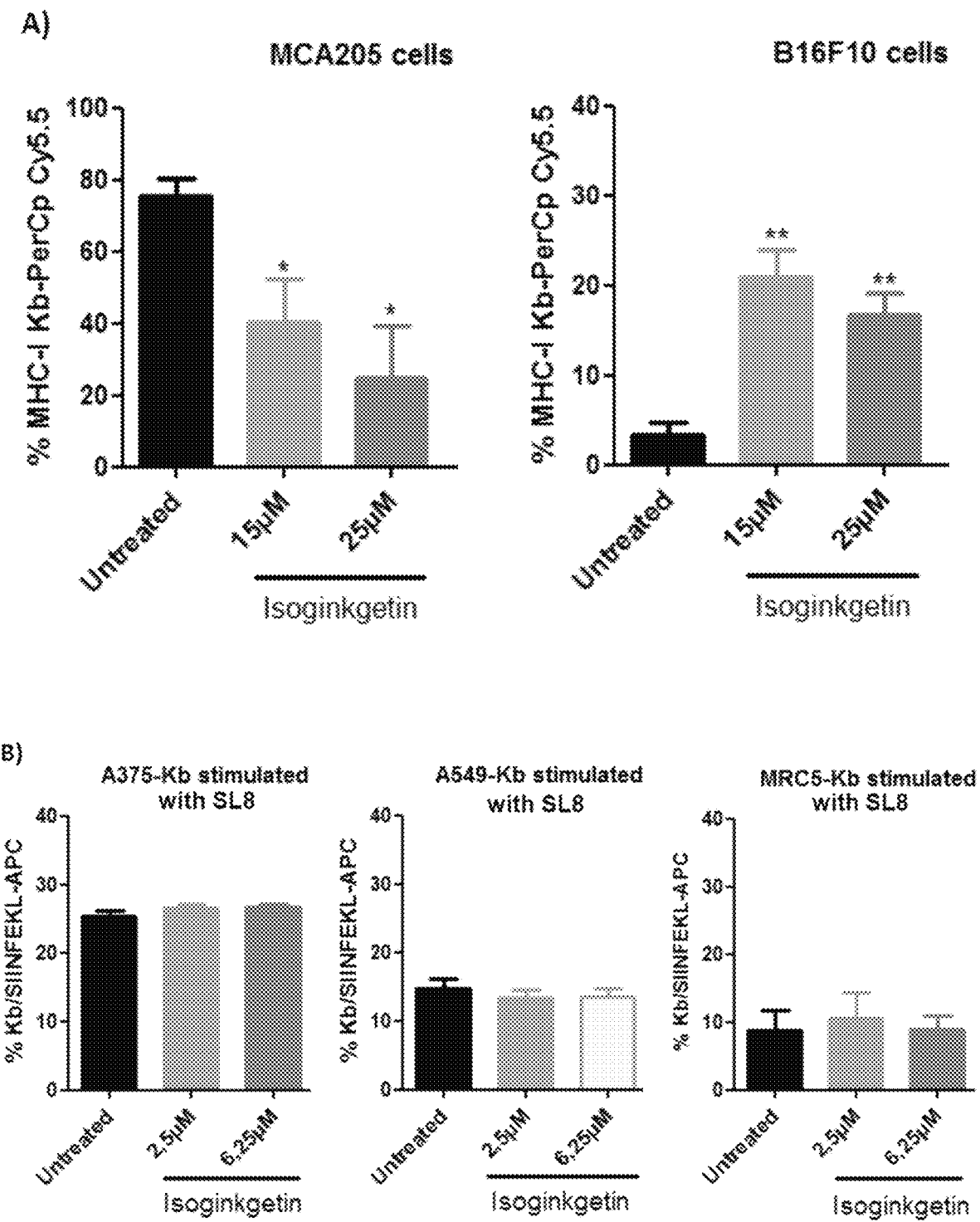

FIG. 8: Expression of H2-K$^b$ molecules at the cells surface.

Flow cytometry analyses of H2-K$^b$ expression on MCA205 and B16F10 cells treated with (A) isoginkgetin. Flow cytometry analyses of transiently expressed H2-K$^b$ expression on A375, A549 and MRC5 cells treated with (B) isoginkgetin.

Figure 9:
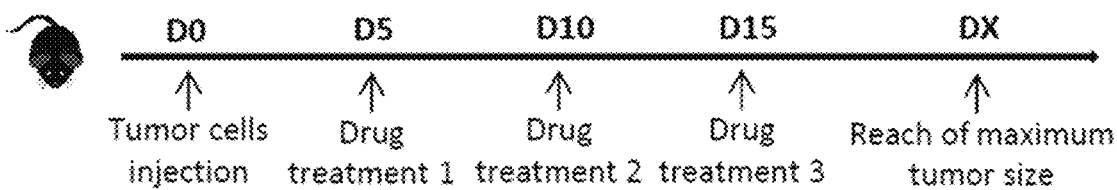
Figure 9:
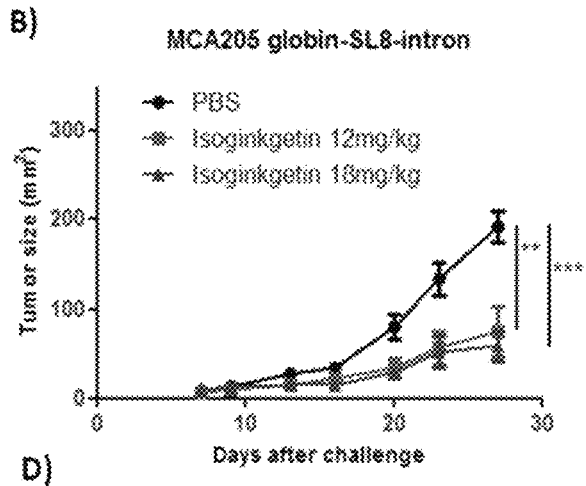
Figure 9:
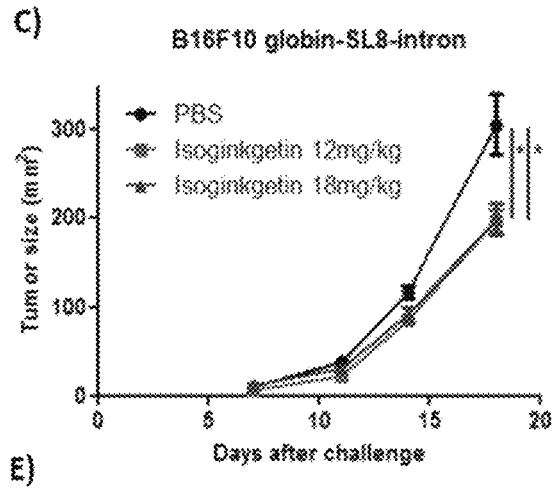
Figure 9:
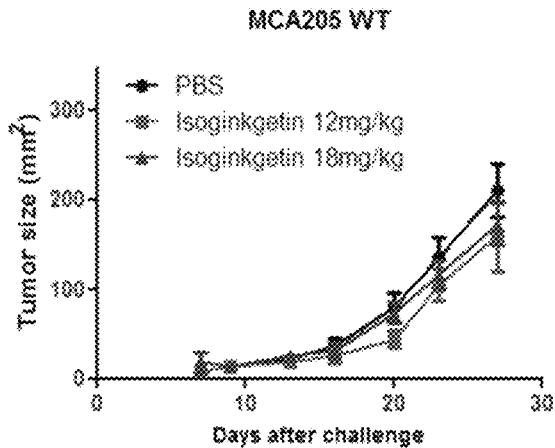
Figure 9:
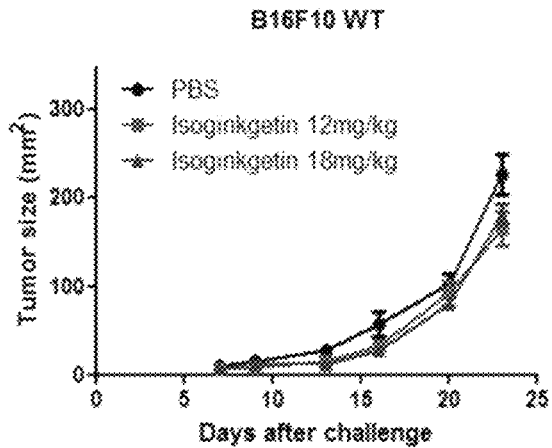
Figure 9:
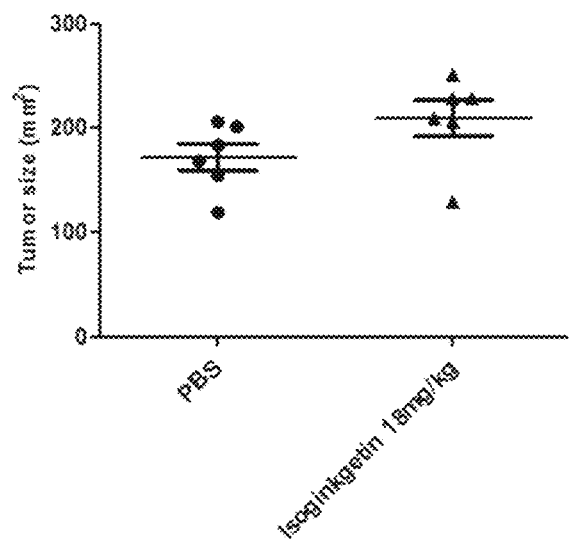
Figure 9:
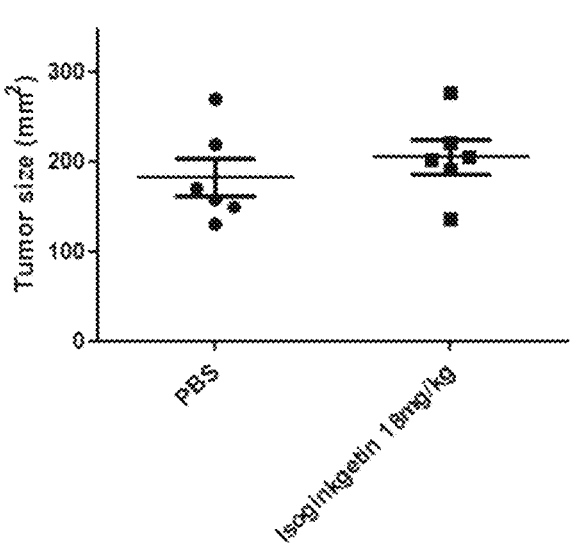
Figure 9:
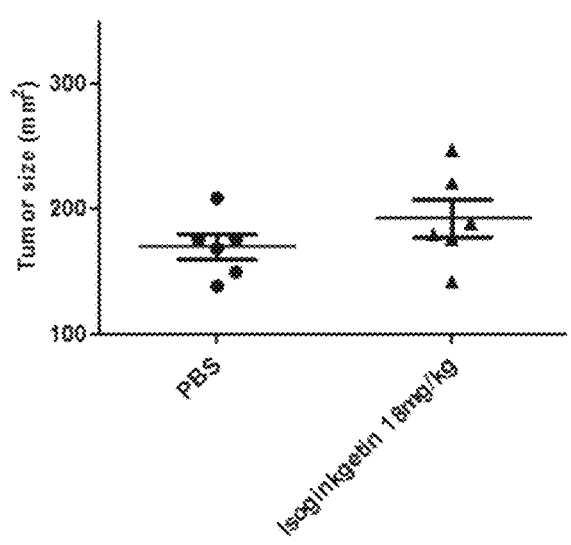
Figure 9:
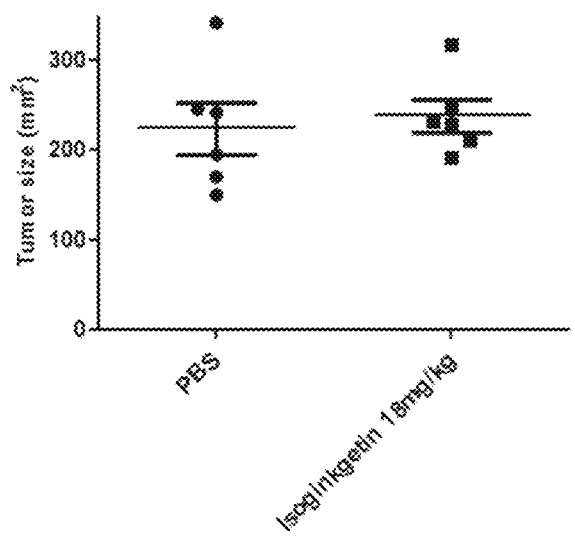

FIG. 9: Isoginkgetin splicing inhibitor reduces the growth of tumor bearing intron-derived-SL8 in an immune-dependent manner.

(A) Experimental settings. Growth of (B) sarcoma MCA205 or (C) melanoma B16F10 cells that both stably express the globin-SL8-intron construct or (D) MCA205 Wild Type (WT) or (E) B16F10 WT cells that were subcutaneously inoculated on the flank of immunocompetent C57BL/6 mice injected intraperitoneally with 12 mg/kg or 18 mg/kg of isoginkgetin at days 5, 10 and 15 after inoculation. Tumor size was assessed every 3 to 4 days until reaching the established ethical endpoints. Each line represents the tumor size in area (mm$^2$) of 6 mice in each group. Size in area (mm$^2$) of (F) MCA205 globin-SL8-intron, (G) B16F10 globin-SL8-intron, (H) MCA205 WT or (I) B16F10 WT tumors subcutaneously inoculated on the flank of immunodeficient Nu/Nu Nude mice injected intraperitoneally with 18 mg/kg of isoginkgetin at days 5, 10 and 15 after inoculation. Data are presented at the day before the endpoints are reached.

Data are given as mean ±SEM. *p<0.05, **p<0.01 (ANOVA with Tukey's multiple comparison test comparing all groups).

Figure 10:
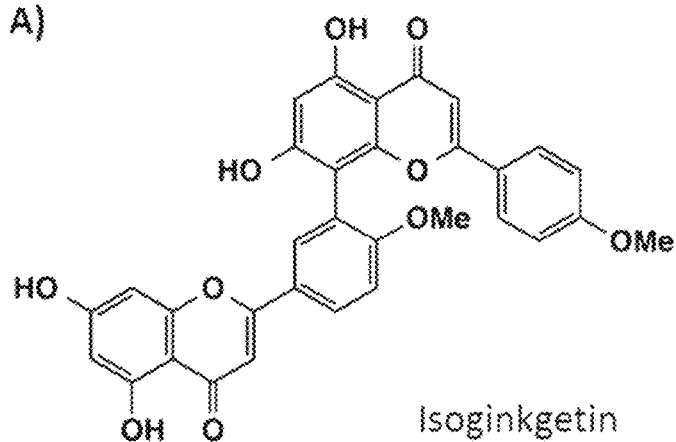
Figure 10:
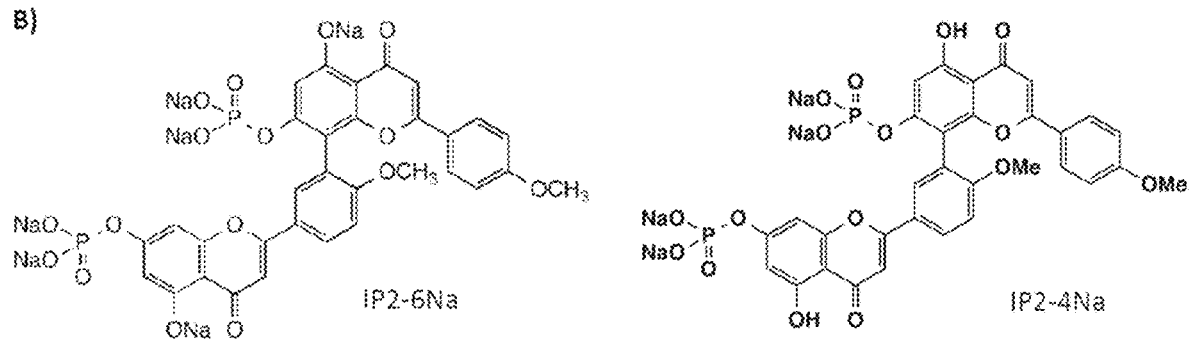
Figure 10:
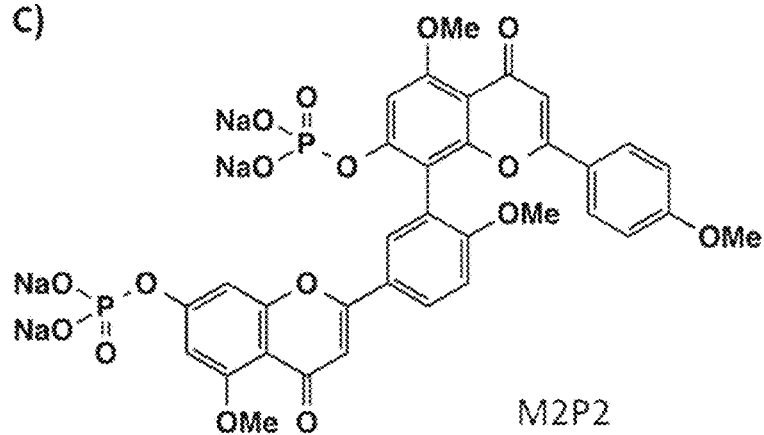
Figure 10:
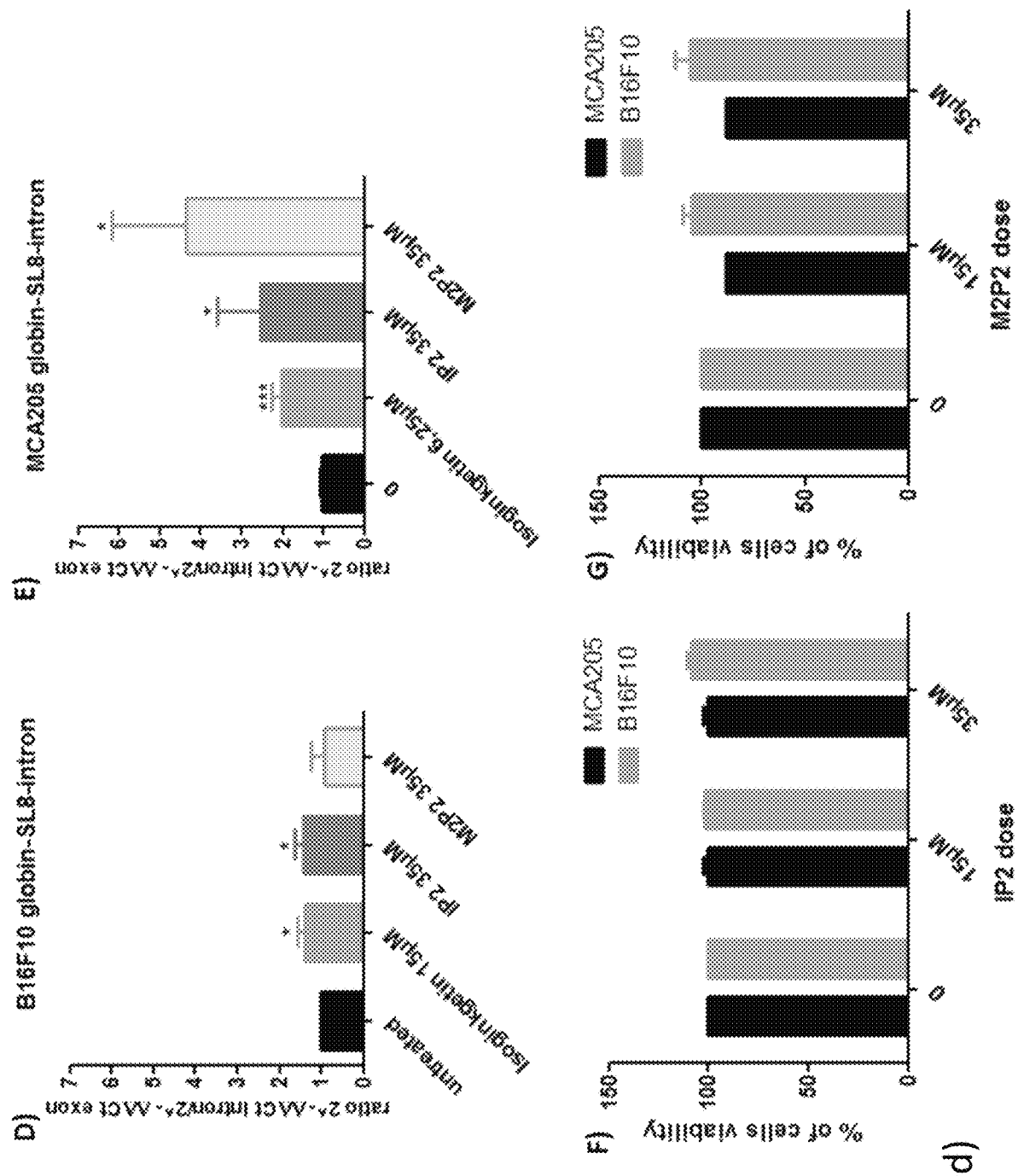

FIG. 10: Synthesis and activity of the isoginkgetin derivatives IP2 and M2P2 (also herein identified as "IM2P2").

Molecular structure of (A) isoginkgetin, (B) IP2 (IP2-6Na and IP2-4Na) and (C) M2P2 compounds. (D) B16F10 globin-SL8-intron or (E) MCA205 globin-SL8-intron were treated with 15 μM isoginkgetin, 35 μM IP2 or 35 μM M2P2 for 48 hours. RNA was extracted and qRT-PCR was performed with primers amplifying the unspliced (intron) and the spliced (exon) globin-SL8-intron RNA. Data are given as mean ±SEM of the ratio of $2^{-\Delta\Delta Ct}$ intron and $2^{-\Delta\Delta Ct}$ exon of at least three independent experiments. MTT assay performed on MCA205 or B16F10 cells treated with 15 μM or 35 μM of (F) IP2 or (G) M2P2. Data are express as mean ±SEM of the percentage of viable cells compared to the control condition of at least three independent experiments. *P<0.05, P<0.01, *P<0.001 (unpaired student t test).

Figure 11:
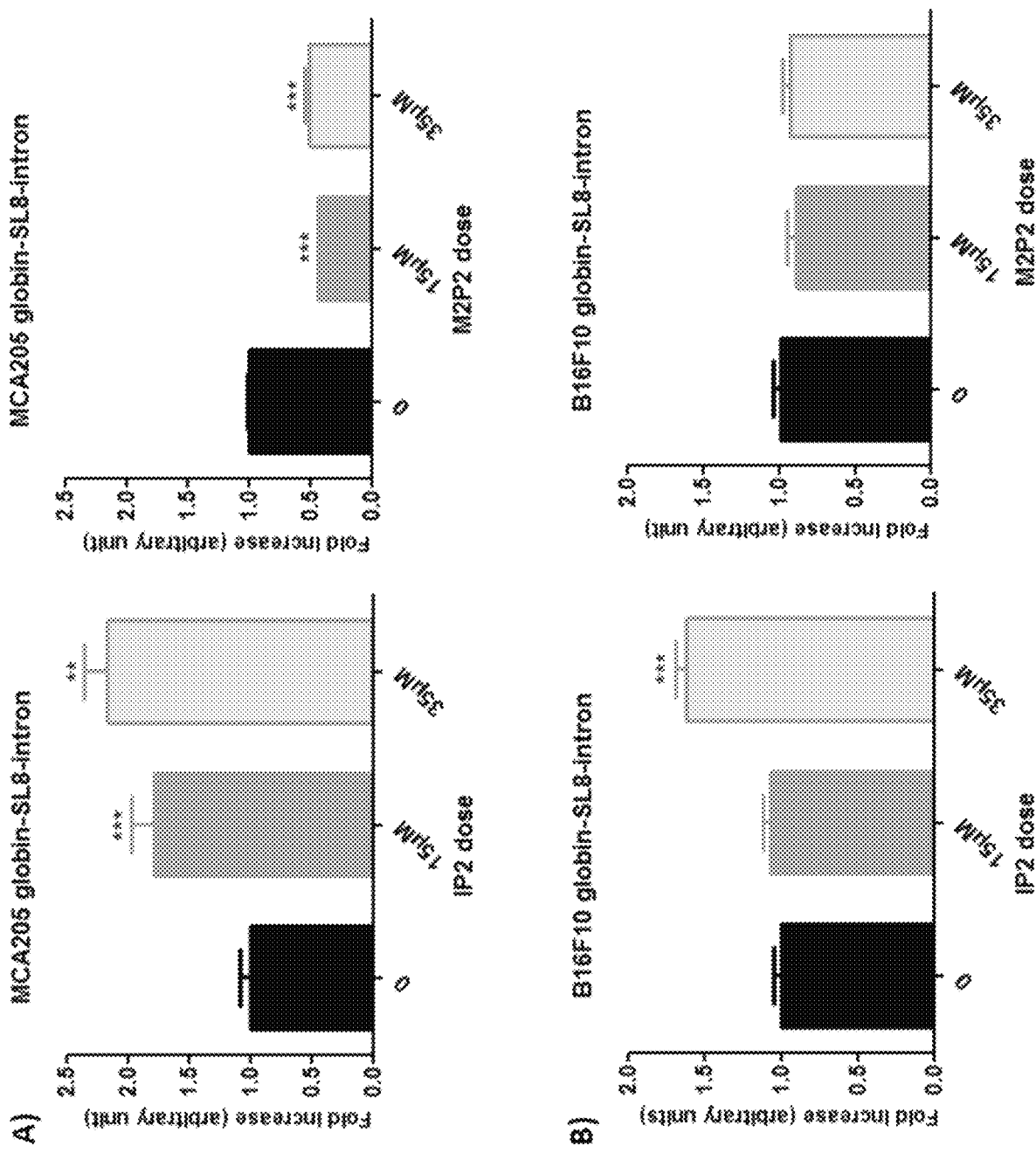
Figure 11:
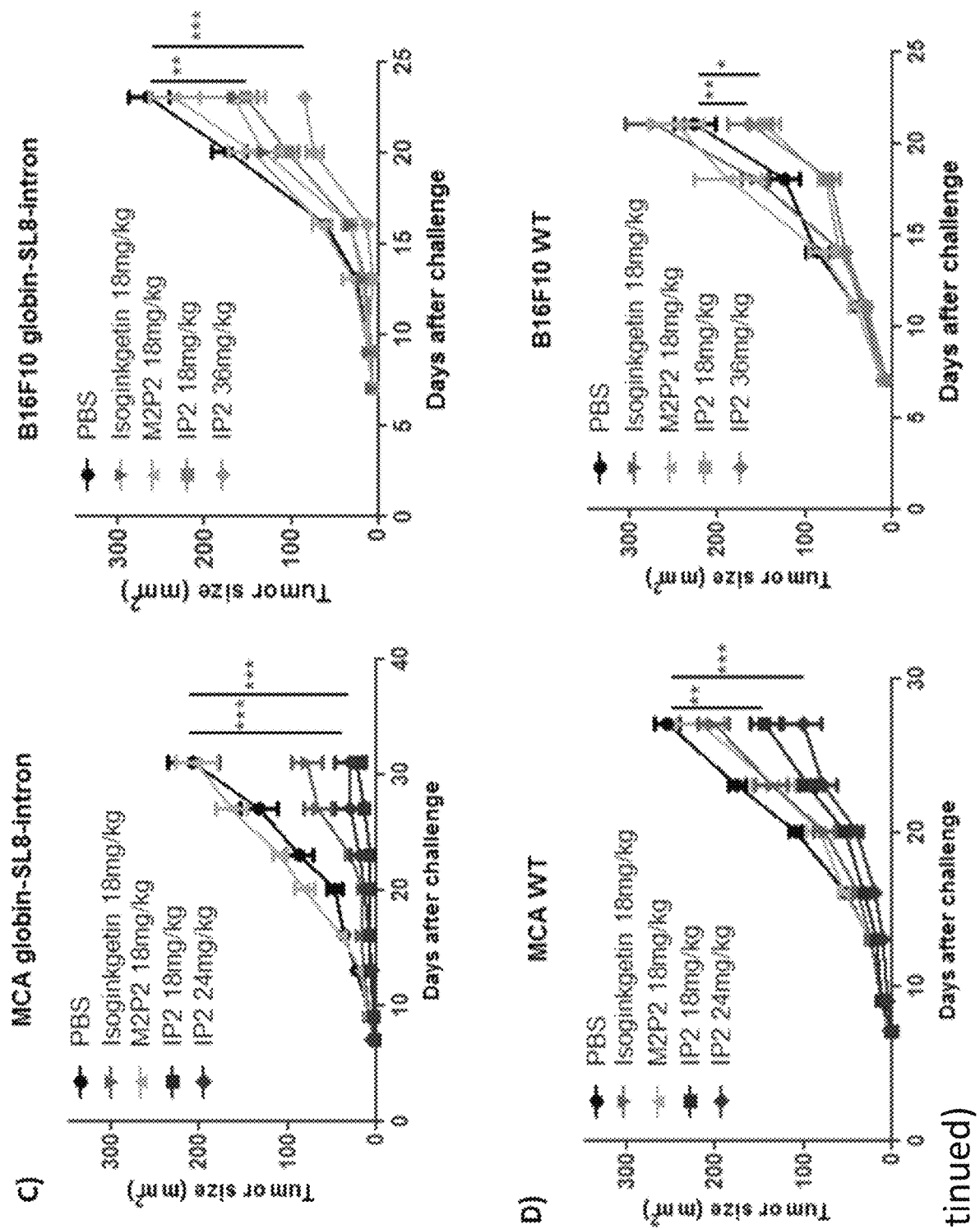
Figure 11:
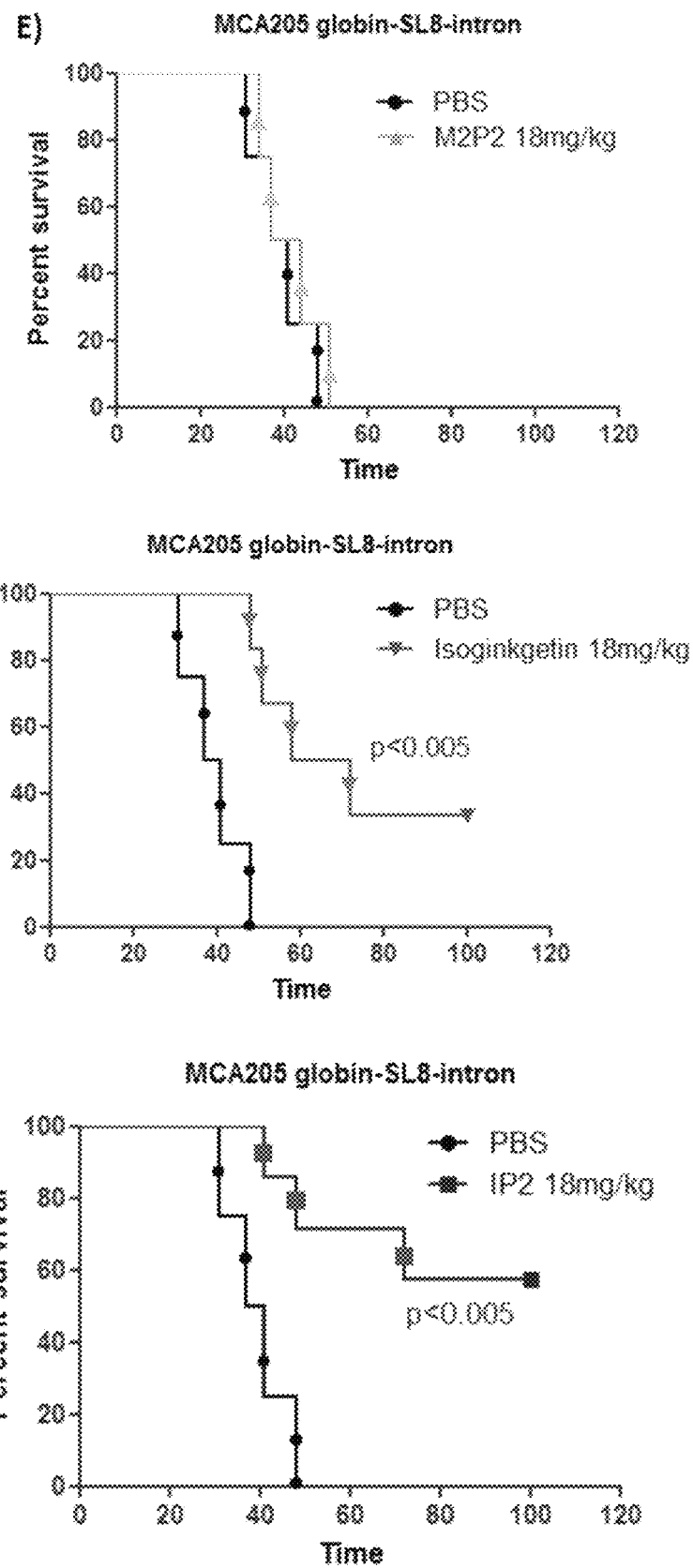

FIG. 11: IP2 treatment reduces tumor growth and extends survival.

B3Z SL8-specific T-cell activation after co-culture with mouse (A) sarcoma MCA205 or (B) melanoma B16F10 cell lines both transiently expressing the intron-derived SL8 peptide and treated upstream with 15 μM or 35 μM of IP2 (left panels) or of M2P2 (right panel). Data are given as mean ±SEM. *P<0.05, P<0.01, *P<0.001 (unpaired student t test). Growth of (C) MCA205 (left panel) or melanoma B16F10 cells (right panel) that both stably express the globin-SL8-intron construct or (D) MCA205 WT (left panel) or B16F10 WT (right panel) cells that were subcutaneously inoculated on the flank of immunocompetent C57BL/6 mice injected intraperitoneally with 18 mg/kg of isoginkgetin, of M2P2 or of IP2 or 24 mg/kg or 36 mg/kg of IP2 at day 5, 10 and 15 after inoculation. Tumor size was assessed every 3 to 4 days until reaching the established ethical endpoints. Each line represents the tumor size in area (mm$^2$) of at least 6 mice in each group. Data are given as mean ±SEM. *p<0.05, **p<0.01 (ANOVA with Tukey's multiple comparison test comparing all groups). Kaplan Meier plots of (E) MCA205 globin-SL8-intron cells inoculated subcutaneously on the flank of immunocompetent C57BL/6 mice injected intraperitoneally with PBS or 18 mg/kg of isoginkgetin, of M2P2 or of IP2. A Log-rank (Mantel-Cox) test was performed.

Figure 12:
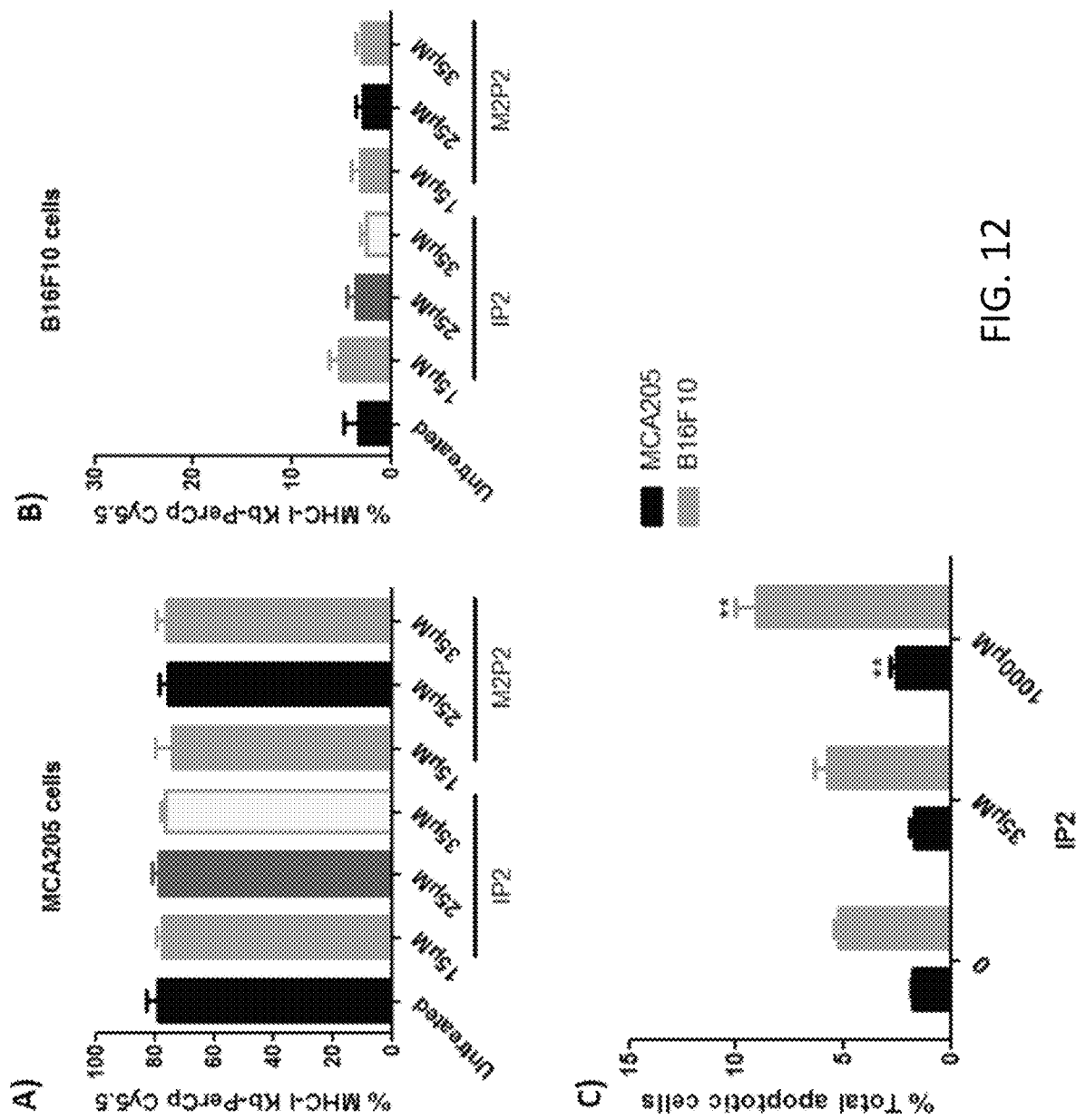

FIG. 12: IP2 does not impact H2-K$^b$ molecules expression at the cell surface and does not induce apoptosis Flow cytometry analyses of H2-K$^b$ expression on (A) MCA205 and (B) B16F10 cells treated with IP2 and M2P2. (C) Flow cytometry analyses of early, late and total apoptotic MCA205 and B16F10 cells treated with 35 μM or 1000 μM IP2 for 18 hours.

Figure 13:
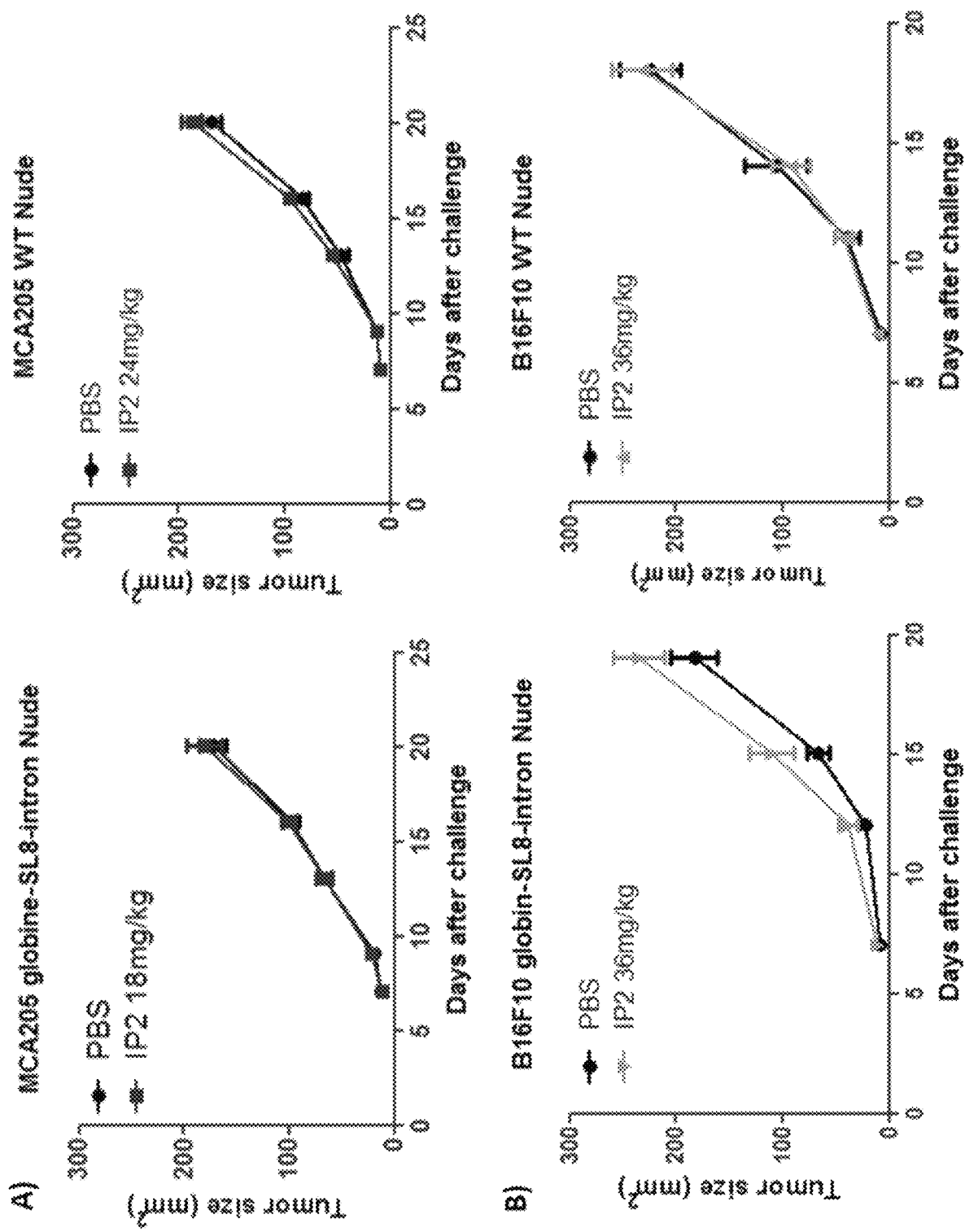
Figure 13:
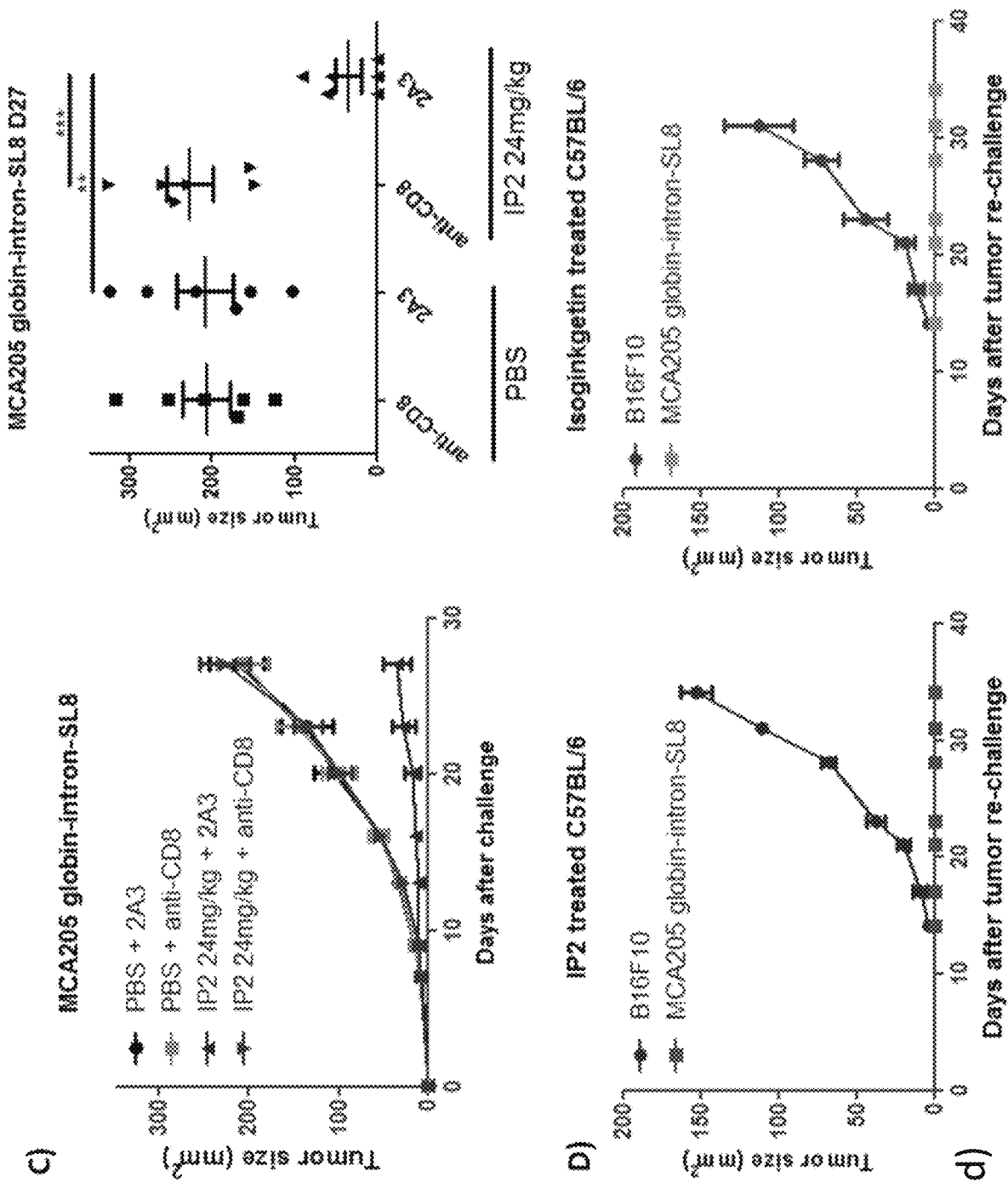

FIG. 13: IP2 therapeutic effect is dependent on the immune response

Growth curve of (A) MCA205 globin-SL8-intron (left panel), MCA205 WT (right panel), (B) Bl6F10 globin-SL8-intron (left panel) or B16F10 WT (right panel) subcutaneously inoculated on the flank of immunodeficient Nu/Nu Nude mice, intraperitoneally injected at days 5, 10 and 15 with 18, 24 or 36 mg/kg of IP2. Growth curve of (C, left panel) MCA205 globin-SL8-intron subcutaneously inoculated on the flank of immunocompetent mice treated with PBS or 24 mg/kg of IP2 at day 5, 10 and 15 after inoculation as well as with in vivo anti-CD8 or isotype every 3 days. Each line represents the tumor size in area (mm$^2$) of at least 6 mice in each group. The C right panel represents the tumor size at day 27. Data are given as mean ±SEM. *p<0.05, **p<0.01 (ANOVA with Tukey's multiple comparison test comparing all groups). (D) Growth curve of MCA205 globin-SL8-intron cells or B16F10 WT cells inoculated in 100 days tumor free C57BL/6 mice previously inoculated with MCA205 globin-SL8-intron and treated with IP2 (left panel) or isoginkgetin (right panel). Each line represents the tumor size in area (mm$^2$) of at least 4 mice in each group.

Figure 14:
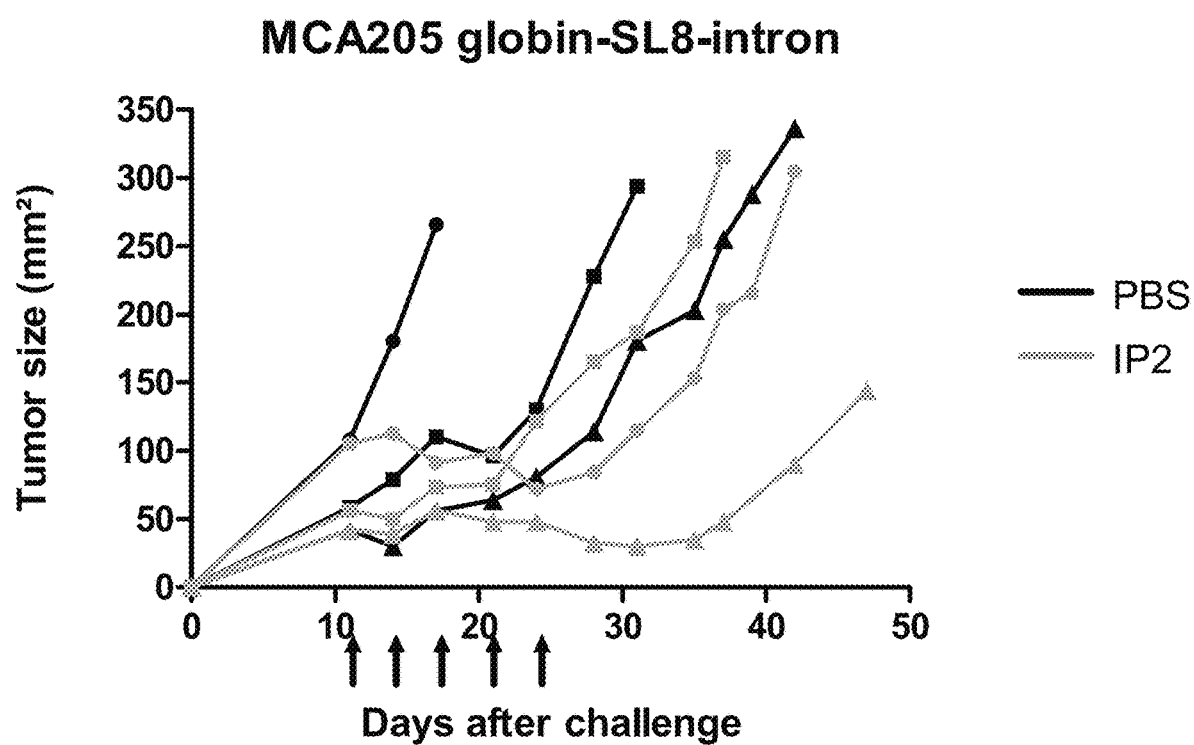

FIG. 14: IP2 treatment reduces tumor growth from established tumor

Growth of sarcoma 15*10$^5$ MCA205 cells that stably express the globin-SL8-intron construct were subcutaneously inoculated on the flank of immunocompetent C57BL/6 mice. Tumors were allowed to progress 10 days before being ranked and assigned to groups of equivalent tumor burden. Three groups of 6 mice were made according to tumor size one group with a tumor size of 40 mm$^2$ (square), one with a tumor size of 50 mm$^2$ (triangle) and one with a tumor size of 100 mm$^2$ (circle). At day 11 all mice were injected intraperitoneally with 24 mg/kg of IP2-4Na. This treatment was repeated 5 times every 3 to 4 days. In parallel, tumor size was assessed every 3 to 4 days until reaching the established ethical endpoints. Each line represents the tumor size in area (mm$^2$) of 6 mice in each group.

EXAMPLES

Materials & Methods

Cell culture

MCA205 mouse sarcoma cell line is cultured at 37° C. under 5% $CO_2$ in RPMI 1640 medium (Life Technologies) in the presence of 1% glutamine, 1% sodium pyruvate, 1% non-essential amino-acids, 1% penicillin/streptomycin and 10% FBS (Life Technologies) under standard conditions. B16F10 mouse melanoma cell line, MRC5 human fibroblast cell line and A375 human melanoma cell line are cultured at 37° C. under 5% $CO_2$ in DMEM medium (Life Technologies) containing 1% glutamine, 1% penicillin/streptomycin and 10% FCS under standard conditions. A549 human lung carcinoma cell line is cultured at 37° C. under 5% $CO_2$ in DMEM/F12+Glutamax I in the presence of 1% Hepes, 1% sodium pyruvate and 10% FBS under standard conditions.

Stable MCA205-Globin-SL8-intron cell line are cultured under the same condition as MCA205 cell line with additional 2 mg/ml G418 (geneticin from Life Technologies) for selection. Stable B16F10-Globin-SL8-intron cell line are cultured under the same condition as B16F10 cell line with additional 2 mg/ml G418 (geneticin from Life Technologies) for selection. The SL8/Kb-specific (B3Z) T-cell reporter hybridoma are cultured at 37° C. under 5% $CO_2$ in RPMI 1640 medium (Life Technologies) in the presence of 1% glutamine, 0.1% β-galactosidase, 1% penicillin/streptomycin and 10% FCS under standard conditions.

T-Cell Assay

MCA205 and B16F10 mouse cell lines are transfected with the plasmid YFP-Globin-SL8-intron or with the PCDNA3 empty plasmid (negative control) with the transfection reagent jetPRIME (Ozyme) or GeneJuice (Millipore) respectively according to each manufacturer protocol. A375, A549 and MRC5 human cell lines are transfected with the plasmid encoding mouse H2-Kb molecule for 12 hours followed by the transfection of the plasmid YFP-Globin-SL8-intron with the transfection reagent jetPRIME (Ozyme) according to the manufacturer protocol. Twenty-four hours after transfection, cells are treated with different doses of Isoginkgetin (Merk Millipore), IP2 or IM2P2 (also herein identified as "M2P2") overnight. Then cells are washed three times with PBS 1X and $5 \times 10^4$ cells are co-cultured with $1 \times 10^5$ B3Z cells. In positive control wells, 4 µg/ml of synthetic peptide SL8 is added. Cells are then incubated at 37° C. with 5% $CO_2$ overnight. Cells are centrifuged at 1200 rpm for 5 min, washed twice with PBS 1X and lysed for 5 min at 4° C. under shaking with the following lysis buffer: 0.2% TritonX-100, 0.2% DTT, 0.5M K2HPO4, 0.5M KH2PO4. The lysate is centrifuged at 3000rpm for 10min and the supernatant is transferred to a 96-well optiplate (Packard Bioscience, Randburg, SA). The revelation buffer containing 33 mM of methylumbellifery β-D-galactopyranoside (MUG) is added and the plate is incubated at room temperature for 3 hours. Finally, the β-galactosidase activity is measured using the FLUOstar OPTIMA (BMG LABTECH Gmbh, Offenburg, Germany). Results are expressed as mean ±SEM. *P<0.05, P<0.01, *P<0.001 (unpaired student t test).

Tumor Challenge and Treatment

C57B1/6J female mice are obtained from Harlan. NU/NU nude mouse mice are obtained from Charles River. At 7 weeks old, mice are injected subcutaneously on the right flank with $5 \times 10^4$ MCA205-Globin-SL8-intron cells or with $4 \times 10^4$ B16F10-Globin-SL8-intron cells along with matrigel (VWR). Five days after challenge, mice are treated intraperitonealy with PBS, Isoginkgetin (Merk Milllipore), IP2 or IM2P2. Fifteen days after challenge mouse are again treated intreaperitonealy with the same drug. Area of the tumor is recorded every 3 to 4 days until day 27. All animal experiments were carried out in compliance with French and European laws and regulations. Results are expressed as mean ±SEM. *p<0.05, P<0.01, *P<0.001 (ANOVA with Tukey's multiple comparison test comparing all groups).

Results

Isoginkgetin Treatment Increases Antigenic Presentation of Intron-Derived Antigens in Cancer Cells.

In recent studies inventors have shown that Pioneer Translation Products ("PTPs") are a major source of peptides for the endogenous MHC class I pathway in vitro. In order to modulate the presentation PTPs-derived antigens at cancer cells surface, they tested the impact of isoginkgetin treatment on the melanoma A375, the lung carcinoma A549 and on the normal fibroblast lung MRC5 cell lines. For that purpose all the cells were transiently expressing respectively the MHC class I $K^b$ molecule and the SL8 epitope from an intron within the β-Globin gene constructs. As shown in FIGS. 1A, 1B and 1C, the natural Isoginkgetin compound causes an increase in intron-PTPs-dependent antigen presentation in cancer cell lines tested, with a dose dependent effect. Similarly, the same experiment has been performed on mice tumor cell lines, one melanoma (B16F10) and one sarcoma (MCA205) cell lines. Both murine cell lines were transiently expressing the PTPs-SL8 epitope derived from an intron within the β-Globin gene construct. Consistent with the previous results in human cell lines, the Isoginkgetin elicits an increase in the PTPs-dependent antigen presentation, with a dose dependent effect in mouse cell lines. These results show that production and presentation of PTPs antigens or PTPs-derived antigens can be positively modulated in cancer cell lines upon isoginkgetin treatment. They support the hypothesis that this molecule could be used as positive immunomodulator to potentiate a specific anti-tumoral immune response dependent on the PTPs production and presentation.

Splicing Event is Required for an Efficient Increase of Exon and Intron-Derived Antigenic Presentation in Cancer Cells after Isoginkgetin Treatment.

The fact that Isoginkgetin increases the presentation of the SL8 epitope at the cell surface from an intron encoded region support the idea that pre-mRNAs are a source for antigen presentation when the spliced machinery is unpaired. Inventors then speculate that the Isoginkgetin will also elicit an increase of antigenic epitope from an exon encoded region, but not from a cDNA construct that does not need to be spliced. For that purpose, both murine cell lines mentioned above were transiently expressing the PTPs-SL8 epitope from an exon within the β-Globin gene construct or transiently expressing the Ova cDNA where the SL8 epitope is found in its right seeting. As expected, the natural Isoginkgetin compound causes an increase in exon and intron-PTPs-dependent antigen presentation in cancer cell lines tested, with a dose dependent effect (FIGS. 2A, 2B, 2D and 2E), whereas the splicing inhibitor has no effect on the production of the SL8 epitope encoded by the Ova cDNA construct (FIGS. 2C and 2F). These results show that splicing is required for isoginkgetin to act as a booster of the PTPs antigens or PTPs-derived antigenic presentation in cancer cells.

Isoginkgetin treatment slows clown tumor growth in vivo.

The above results demonstrate that independently of the source of PTPs-dependent antigen encoded by exon or intron sequences, the natural product of Isoginkgetin is able to increase their production and presentation in vitro at the cell surface of treated tumor cell lines. The next evident question was to see if the Isoginkgetin, which has to be dissolved in DMSO, can have the same effect on tumor growth and $CD8^+$ T cell proliferation in vivo. For that purpose, MCA205 sarcoma cells stably expressing the SIINFEKL (SL8) epitope from an intron in the β-Globin gene (Globin-intron-SL8) were subcutaneously inoculated in mouse. Five days after this inoculation, the mice were intraperitoneally vaccinated with a define dose of Isoginkgetin. Then, 10 days later the same dose was again injected. During that time the tumor growth was monitored every two to three days (FIG. 3A). Inventors observed a significant 50% reduction of tumor growth at day 27 after challenge in mice treated with 6, and 18 mg/kg of Isoginkgetin (FIG. 3B).

In order to assess the requirement of the immune response for this effect, they tested the impact of 18 mg/kg isoginkgetin treatment in immunodeficient nu/nu mice with the same settings as previously described and observed that it has no effect on the tumor growth (FIG. 4D). These results show that tumor size reduction upon isoginkgetin treatment requires the presence of an active immune response in vivo. Inventors next decided to generate derivatives of the Isoginkgetin in order to try to increase the anti-tumor response. In fact, isoginkgetin is insoluble in water and can only be dissolved in DMSO solvent rendering its pharmacokinetic in the peritoneal cavity less efficient.

Derivative Compounds from the Natural Isoginkgetin Product: Schema of Synthesis.

In order to make isoginkgetin available for broader in vivo validation without the use of toxic carriers or cosolvents (DMSO), it was considered necessary to find a strategy to enhance its solubility. The compounds of the invention were prepared from commercially isoginkgetin, a small polyphenolic molecule more commonly referred to as biflavonoid, extracted from leaves of maidenhair tree, *Ginko biloba L.* Taking in account that the natural products dissolved in DMSO might not be well assimilated in mouse, inventors decided to generate derivative compounds that will have kept their functions, meaning inhibitor of spliceosome and positive immunomodulators against cancer cell lines with a better pharmacokinetics than the natural compound dissolve in a cosolvent.

The synthesis of IP2 compounds (2 and 2'), depicted in Scheme 1 (FIG. 5), was accomplished from isoginkgetin by phosphorylation employing in situ formation of diethylchlorophosphite to provide 1. Further cleavage of the ethyl ester protective groups with iodotrimethylsilane afforded the phosphoric acid intermediate, which was immediately treated with sodium hydroxide to complete a practical route to the disodium phosphate prodrugs 2 and 2'. The water solubility of 2 and 2' was found to be considerably higher than that of the parent compound isoginkgetin.

The synthesis of IM2P2, derivative 4, was accomplished as depicted in Scheme 1. The remaining two phenol groups of 1 were alkylated using methyl iodide to furnish compound 3. Treatment of this latter under similar conditions to prepare 2 and 2' from 1 gave the disodium phosphate prodrug 4, whereas its reaction under basic conditions provided compound 5.

The prodrug 8 was synthesized in three steps from 6 by phosphorylation of phenol groups in the C4 position followed by cleavage of the ethyl groups of 7 with trimethylsilyl iodide and reaction of the resulting phosphoric acid with sodium hydroxide in water to afford the sodium phosphate prodrug 8.

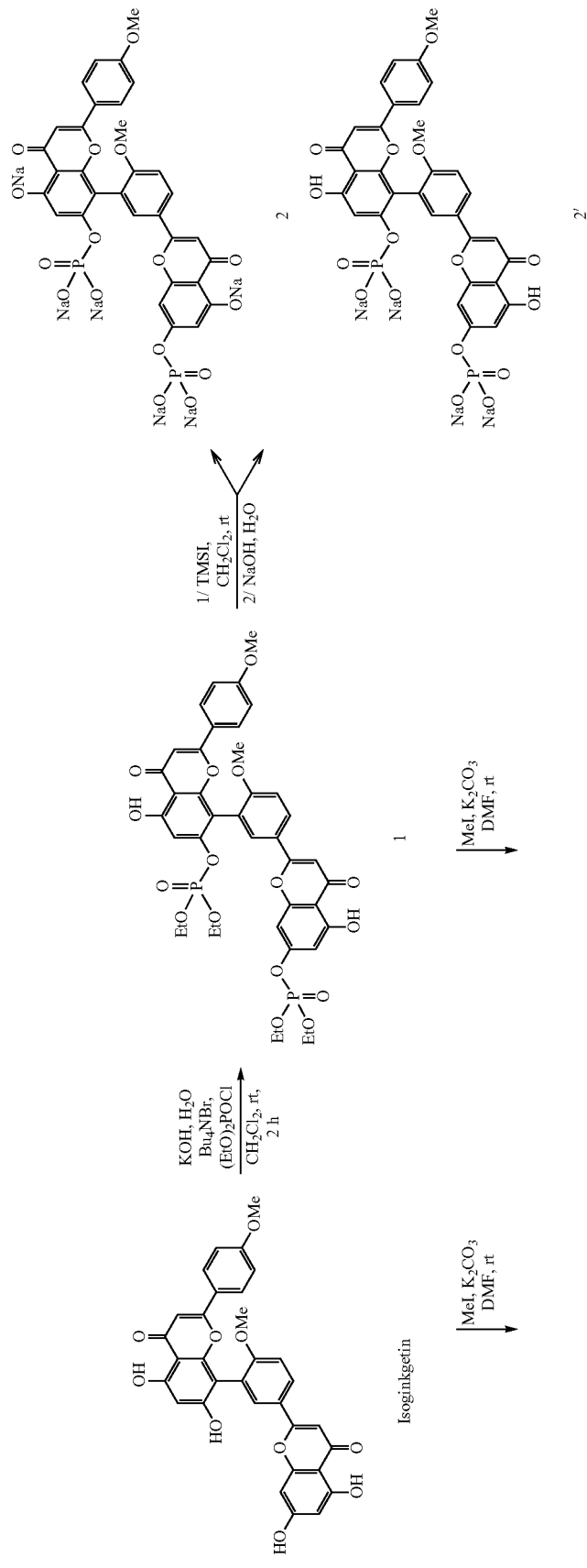

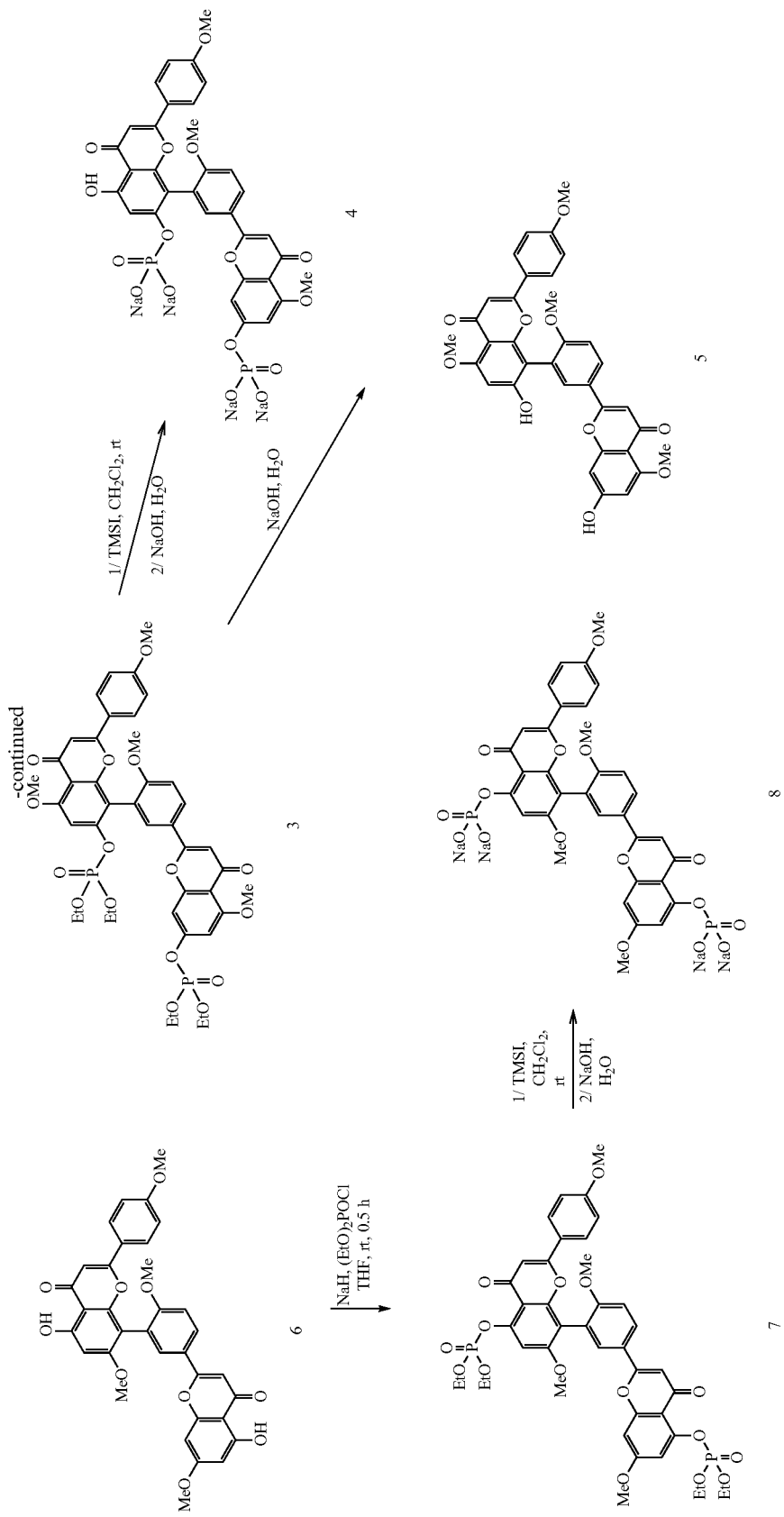

Treatment of isoginkgetin with a large excess of methyl iodide (5 equiv) under basic conditions furnished fully methylated compound 11 [cf. Scheme 2 (FIG. 6)]. The use of 3 equivalents of MeI produced a mixture of trialkylated products 9 and 10 which were easily separated by column chromatography. Reaction of isoginkgetin with pyridinium chloride allows ether cleavage and afforded the polyphenolic compound 12.

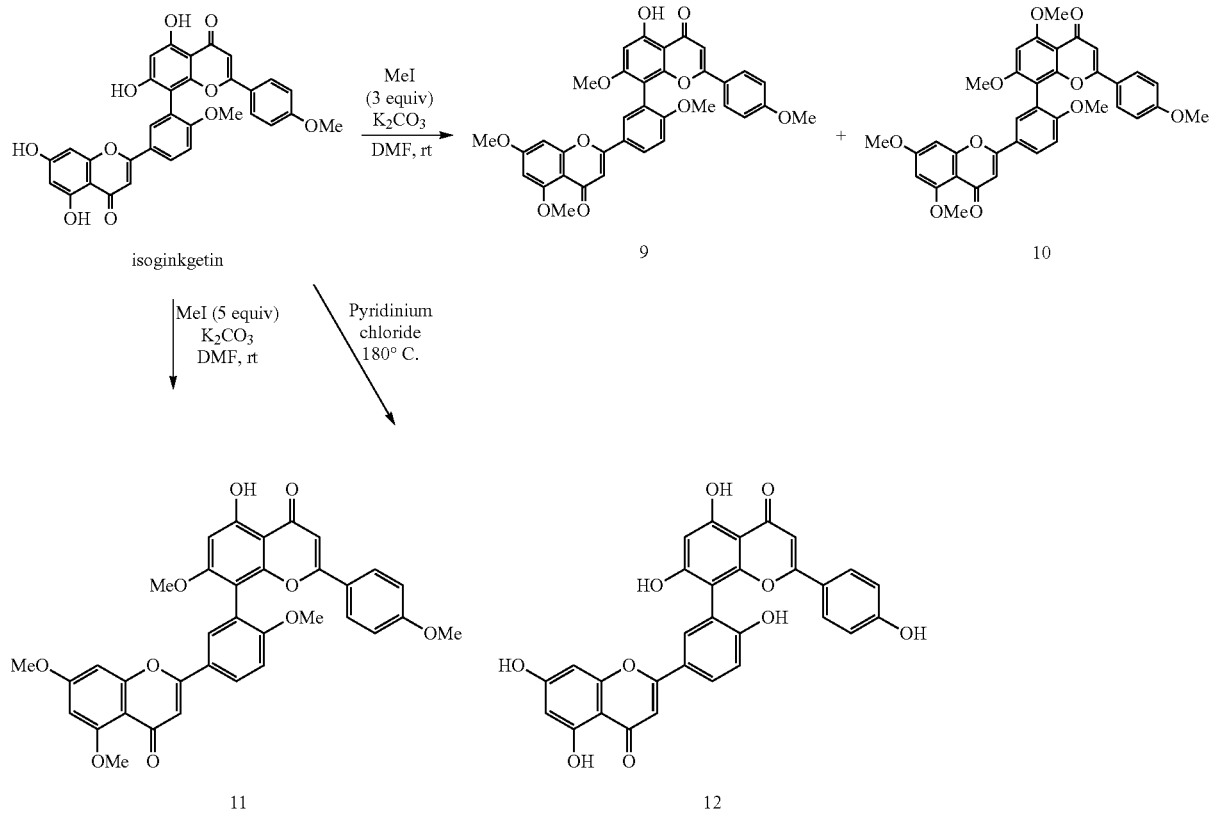

Scheme 2 (cf. FIG. 6)

Isoginkgetin Derivative IP2 Efficiently Increases MHC Class I Presentation of Intron-Derived Antigen in Vitro and Dramatically Reduces Tumor Growth in vivo in an Immune-Dependent Manner.

In order to test the new compounds as positive immunomodulators against tumor cell lines, inventors first decided to test them in an in vitro assay. Both the derivatives 2 and/or 2', both also herein identified as "IP2", and the derivative 4, called "IM2P2", were able to be dissolved in water. After treatment of MCA205 cells transiently expressing PTPs-SL8 epitope derived from an intron in the β-Globin gene (Globin-intron-SL8) with 15 μM, 25 μM or 35 μM of IP2, inventors observe an increase in PTPs-dependent antigen presentation (FIG. 4A). On the contrary, treatment of MCA205 cells expressing inventors' PTPs-encoded construct with 15 μM, 25 μM and 35 μM of IM2P2 (FIG. 4B) or the product or compound 10 (FIG. 4C) does not increase the presentation of inventors' PTPs-derived antigen. Then, inventors decided to look in vivo at the effect of these derivatives in term of anti-tumor growth and inducers of specific anti-tumor immune responses. For that purpose, MCA205 sarcoma cells, stably expressing the SIINFEKL (SL8) epitope from an intron setting in the β-Globin gene (Globin-intron-SL8), were subcutaneously inoculated in mice. Then, 5 days after this inoculation, each group of mice were respectively intraperitoneally vaccinated with 18 mg/kg of Isoginkgetin, IP2 or IM2P2. Ten days later, the same dose of each compound was again injected. During that time the tumor growth was monitored every two to three days (FIG. 3A). In the group of mice treated with 18 mg/kg of IP2, inventors observed a dramatical decrease of tumor growth compared to the group of mice treated with 18 mg/kg of Isoginkgetin (FIG. 4D). In parallel and on the contrary, mice that were treated with 18 mg/kg of IM2P2 did not demonstrate any tumor growth decrease (FIG. 4D).

To demonstrate that the tumor growth decrease is due to specific anti-tumor immune responses in a PTPs-dependent manner, inventors looked at the effect of the compounds in Nu/Nu athymic nude mice. For that purpose, MCA205 sarcoma cells stably expressing the SIINFEKL (SL8) epitope from an intron setting in the β-Globin gene (Globin-intron-SL8) were subcutaneously inoculated in mouse. Then, 5 days after this inoculation, each group of mice were respectively intraperitoneally vaccinated with 18 mg/kg of Isoginkgetin, IP2 and IM2P2. Then 10 days later the same dose of each compound was again injected. During that time the tumor growth was monitored every two to three days (FIG. 3A). FIG. 4E shows that any of the compounds used have an effect on the tumor growth of the sarcoma cell lines in these immunodeficient mice, supporting and shedding further light on the fact that the selected derivative of the natural product Isoginkgetin which is a splicing inhibitor can be seen as positive immunomodulator against cancers and can be used as a new chemotherapeutic treatment.

Discussion

The present invention demonstrates for the first time that the product herein identified as IP2 has a very positive effect on the antitumor immune response and therefore on tumor growth. Inventors indeed demonstrated that a specific derivative of the natural product Isoginkgetin is a potent stimulator of the anti-tumor immune response in vitro and also in vivo. Such a small molecule exhibiting this kind of mechanism of action is unprecedented. Inventors' data open the way to new anti-cancer applications within the framework of targeted molecular therapies.

Pre-mRNA splicing is an essential mechanism required for the normal function of all mammalian cells. In the last few years, several studies reported the presence of mutations and overexpression of main spliceosome factors associated with aberrant splicing activity in various cancers. Few years ago, inventors have also provided some evidence that the inhibition of the spliceosome increases MHC class I PTPs-dependent antigen presentation. These findings put the focus on the spliceosome as a potential target in anti-cancer treatment. Small molecules have already been reported to inhibit the spliceosome and specifically to inhibit the spliceosome factor SF3B1 function. Although the precise mechanisms of these small molecules are not yet completely understood, it has been reported that they can be effective in cancer therapy by reducing tumor size from 40 to 80% depending of the compound used. The only one to date that has been tested in human is the E7107. It has been stopped because of problems of toxicity. This compound is known to inhibit the spliceosome by interacting with SF3B1. In that study, inventors provide both in vitro and in vivo evidences that by modulating the spliceosome activity using the herein described specific derivative compound IP2 of the natural product Isoginkgetin a specific anti-tumor immune response can be induced.

Instead to look at the effect of these different compounds inhibiting a specific component of the spliceosome inventors decided to look at another class of inhibitors that have been reported to inhibit the formation of the spliceosome complex. Isoginkgetin has been reported to interfere in the early step of assembly of the spliceosome and it has been also reported to be a potent tumor cell invasion inhibitor. In fact, it has been demonstrated that Isoginkgetin inhibits the A complex of the pre-spliceosome to form a larger pre-catalytic spliceosome B complex. Inventors demonstrated that by inhibiting the formation of the spliceosome, as early as possible using derivative IP2 of the Isoginkgetin in vitro and in vivo, the anti-tumor antigenic presentation was increased very significantly, by inducing specifically CD8$^+$ T cell proliferations against PTPs-dependent epitopes. Inventors herein report that IP2 can be used as a new chemotherapeutic agent against cancer, in particular against melanoma and sarcoma.

Additional Results

Splicing Inhibition Increases the Presentation of Antigens Derived from Introns and Exons in Cancer Cells Cancer cells display different intracellular mechanisms that can shape the pool and the quantity of peptides presented on MHC class I (MHC-I) molecules at their surface, leading to reduction of their antigenicity and escape of T-cell recognition. Inventors have shown that PTPs are a major source of peptides for the endogenous MHC-I pathway in vitro. In addition, they have provided the first proof of the positive impact of splicing inhibition on PTPs-dependent antigen presentation by treating HEK cells with the splicing inhibitor isoginkgetin. The latter has been reported to inhibit the spliceosome during the early stages of its assembly. In view to improve antigenicity and immune recognition of cancer cell lines, inventors determined whether isoginkgetin was able to modulate positively the expression and the presentation of tumor associated PTPs-derived antigens (TA-PTPs) at cancer cells surface. For that purpose, the human melanoma cell line A375, the human lung cancer cell line A549 and the normal human fibroblast lung cell line MRC5 were transiently expressing the MHC-I H2-K$^b$ molecule and the PTPs-SL8 epitope from an intron within the β-Globin gene construct (Globin-SL8-intron) and treated with different concentrations of isoginkgetin for 18 h. All results were expressed based on the ratio of B3Z activation with and without extracellular addition of the SL8 peptide in order not to be biased by modulations in the overall expression of the H2-K$^b$ molecules at the cell surface upon treatment. Treatment with isoginkgetin increases intron-derived-SL8 antigen presentation in the three cell types, in a dose dependent manner (FIG. 7A). Concentrations of isoginkgetin used were not toxic for the human cells as the viability is shown to be over 80% upon treatment (table 1).

TABLE 1

Percentage of human cell lines survival after isoginkgetin treatment.

| | | % cell viability (±SEM) | | |
|---|---|---|---|---|
| | Doses (μM) | A375 | A549 | MRC5 |
| Isoginkgetin | 2.5 | 100 | 100 | 100 |
| | 6.25 | 100 | 84 (±1.86) | 100 |

MTT assay on A375, A549 and MRC5 cell lines treated with 2.5 μM or 6.25 μM of isoginkgetin. Dare are given as the mean of the percentage of cell viability ±SEM from at least three independent experiments.

In parallel, the same experiment was performed on the mouse melanoma B16F10 and sarcoma MCA205 cell lines that were transiently expressing the Globin-SL8-intron construct. Consistent with the previous results, the isoginkgetin elicits an increase in the intron-derived-SL8 antigen presentation, in a dose dependent manner (FIG. 7B). Efficient doses lead to cell viability over 50% in these cell lines (table 2).

TABLE 2

Percentage of human cell lines survival after isoginkgetin and treatment.

| | | % cell viability (±SEM) | |
|---|---|---|---|
| | Doses (μM) | MCA205 | B16F10 |
| Insoginkgetin | 6.25 | 84.8 (±9.6) | 86.5 (±2.2) |
| | 15 | 56.3 (±4.9) | 58.6 (±3.8) |
| | 25 | 51.7 (±4.2) | 51.2 (±4.8) |

MTT assay on MCA205 and B16F10 cell lines treated with 6.25 μM, 15 μM or 25 μM of isoginkgetin. Dare are given as the mean of the percentage of cell viability ±SEM from at least three independent experiments.

To investigate further the impact of isoginkgetin on PTPs presentation, both murine sarcoma and melanoma cell lines were transiently expressing the PTPs-SL8 epitope from an exon within the β-Globin gene construct (Globin-SL8-exon)

or transiently expressing the Ova cDNA. In the latter construct, the SL8 epitope is found in its right setting and does not need to be spliced. Inventors observed that the isoginkgetin increases exon-derived-SL8 antigen presentation in the MCA205 and in the B16F10 cancer cell lines with a dose-dependent effect (FIG. 7C), whereas the splicing inhibitor has no effect on the production of the SL8 epitope encoded by the Ova cDNA construct (FIG. 7D). Hence, splicing event seems to be required for isoginkgetin to impact PTPs-dependent antigen presentation. This suggests an action of isoginkgetin during the production step of PTPs and not further down in the MHC-I antigen presentation pathway. Along with these results, inventors showed that the expression of the $H2-K^b$ molecules at the cell surface is affected differently in the cell lines treated with isoginkgetin, i.e. it decreases in MCA205 (FIG. 8A, left panel), increases in B16F10 (FIG. 8A, right panel) and is stable on human cell lines (FIG. 8B).

Overall, these results show that the natural product isoginkgetin acts as a booster of the PTPs-derived antigen presentation in cancer cells independently of the epitope setting, i.e. in exonic or in intronic sequences, and independently of the cell lines tested. This shed light on the importance of the splicing event for the production and the presentation of MHC-I antigens in cancer cells. Finally, inventors' data support the idea that pre-mRNAs are a source for antigen presentation when the spliced machinery is unpaired.

Isoginkgetin Treatment Slows Clown Tumor Growth in vivo when the Intron-Derived-SL8 Epitope is Expressed and its action is Dependent on the Immune Response.

Antigens abundance at the cell surface has been demonstrated to be a key parameter in determining the magnitude of the $CD8^+$ T cell response and hence in defining immunodominance (Doherty et al., 2006). The SL8 peptide has been widely shown to be highly immunogenic in vivo. Looking at SL8-specific T-cells activation in vitro, inventors observed a change in the abundance of the SL8 expression at the cancer cells surface after splicing inhibition. In order to test this hypothesis in vivo, they first looked at the impact of isoginkgetin treatment on the growth of tumors that express the intron-derived SL8 peptide. For that purpose, both MCA205 sarcoma cells and B16F10 melanoma cells that stably express the globin-intron-SL8 construct were inoculated subcutaneously in mice. At days 5, 10 and 15 after tumor inoculation, the mice were injected intraperitoneally with a define dose of isoginkgetin, and the tumor growth was monitored (FIG. 9A). In mice bearing MCA205 globin-SL8-intron (MCA205 GI) tumors, inventors observed a significant reduction of tumor size, over 50% at day 27 after challenge when treated with 12 and 18 mg/kg of isoginkgetin (FIG. 9B). The impact of isoginkgetin treatment on B16F10 globin-SL8-intron (B16F10 GI) tumor growth is lower than on MCA205 GI; however the drug still significantly slows down tumor growth (FIG. 9C). To assess the link between SL8 overexpression and tumor growth reduction in vivo after isoginkgetin treatment, inventors performed the same experiment with mice inoculated with either MCA205 or B16F10 wild type (WT) cells. No significant reduction of MCA205 WT (FIG. 9D) or B16F10 WT (FIG. 9E) tumor growth was observed after treatment with 12 and 18 mg/kg of isoginkgetin. These results suggest that the expression of an immunodominant epitope, herein the SL8 peptide, is required for isoginkgetin to impact tumor growth in vivo.

Inventors then assessed the requirement of the immune response for isoginkgetin to reduce tumor growth Immunodeficient Nu/Nu nude mice were inoculated subcutaneously with either MCA205 or B16F10 cells that stably express the Globin-intron-SL8 or WT, and were treated with the same settings as previously described (FIG. 9A). No effect of isoginkgetin treatment was observed on the growth of each of the four tumor types (FIG. 9F-I).

Overall, these results show that tumor size reduction upon isoginkgetin treatment requires the presence of an active immune response in vivo, and suggest that the increase of the expression of an immunodominant epitope drives the anti-tumor immune response.

The Compound Derivatives from the Natural Isoginkgetin (Product IP2 and Product M2P2, the Last One Being also Herein Above Identified as "IM2P2") are Water Soluble, Inhibit the Splicing and are Less Toxic.

Derivatives of the natural isoginkgetin product were synthesized and tested for their ability to inhibit the splicing, to increase PTPs-derived antigens in vitro as well as for their ability to reduce tumor growth in vivo. The derivatives IP2 (see IP2-6Na and IP2-4Na on FIG. 10B) and M2P2 (FIG. 10C) were synthesized from the commercial isoginkgetin (FIG. 10A), more commonly referred to as biflavonoid, extracted from leaves of maidenhair tree, Ginko biloba L. Schema of synthesis is provided in FIG. 5. Briefly, the synthesis of IP2 or compounds 2 and 2' (as named in the schema) was accomplished by the phosphorylation of isoginkgetin employing in situ formation of diethylchlorophosphite to provide compound 1. Further cleavage of the ethyl ester protective groups with iodotrimethylsilane afforded the phosphoric acid intermediate, which was immediately treated with sodium hydroxide to complete a practical route to the disodium phosphate prodrug. For the synthesis of the M2P2 molecule, the remaining two phenol groups of compound 1 were alkylated using methyl iodide to furnish compound 3. Treatment of the latter under similar conditions to prepare compounds 2 and 2' from compound 1 gave the disodium phosphate prodrug 4 or M2P2, whereas its reaction under basic conditions provided compound 5.

The water solubility of IP2 and M2P2 was found to be considerably higher than that of the parent compound isoginkgetin (data not shown). In addition, inventors tested the ability of IP2 and M2P2 to inhibit the splicing of the Globin-SL8-intron gene product in MCA205 and B16F10 cells. Interestingly, IP2 and M2P2 provide two distinct patterns of splicing inhibition in each cell line. IP2 treatment increases the presence of non-spliced RNA products in both cells, such as isoginkgetin treatment does. In contrast, M2P2 treatment does not impact splicing in B16F10 cells while it has a strong impact on splicing in MCA205 compared to IP2 and isoginkgetin treatment (FIGS. 10D and 10E). Hence, IP2 and M2P2 appear to display different mechanisms for inhibiting the splicing. Importantly, inventors observed that the splicing pattern of IP2 is similar to the one of isoginkgetin for the studied gene product. In addition, it has been shown that cancer cells can acquire deficiencies in the splicing machinery that benefit their growth, for example by preventing the expression of tumor suppressor genes. These deficiencies do not have the same nature in all tumors and therefore could explain the distinct effects of splicing inhibitors on separate tumor types. Both IP2 and M2P2 display no toxicity in MCA205 and B16F10 WT cells at the doses tested (FIGS. 10F and 10G). Overall, inventors have provided and herein identify for the first time two new drugs that are water soluble and that can impact the splicing differently in two distinct model cell lines at doses that do not impact cells viability.

Isoginkgetin Derivative IP2 Efficiently Increases MHC-I Presentation of Intron-Derived Antigen in Vitro, Reduces Tumor Growth in vivo and Extends Survival.

In order to test the potential immunomodulatory effect of IP2 and M2P2 compounds in comparison with isoginkgetin, the two molecules were first tested for their ability to increase the MHC-I presentation of PTPs-derived antigens in vitro. For that purpose, MCA205 and B16F10 cells were transiently expressing the Globin-intron-SL8 construct and treated with 15 μM or 35 μM of IP2 or M2P2. While treatment with IP2 increases the intron-SL8-derived antigen presentation in MCA205 and B16F10 cells similarly to what inventors observed after isoginkgetin treatment (FIG. 11A and B, left panels), M2P2 decreases its presentation in MCA205 cells and does not impact it in B16F10 cells (FIG. 11A and B right panels). These results are interestingly correlated to the respective ability of IP2 and M2P2 to inhibit the Globin-SL8-intron gene splicing. In fact, M2P2 has no impact both on splicing and on the SL8 antigen presentation in B16F10. Conversely, M2P2 strongly inhibits the splicing in MCA205 and negatively affects the SL8 presentation. Along with these results, inventors showed that the expression of the H2-K$^b$ molecules at the cell surface is not affected in the cell lines treated with IP2 and M2P2 (FIGS. 12A and 12B). Hence, it seems likely that a tight regulation of splicing is required for treatments to positively impact the presentation of intron-derived epitopes. These results show that the isoginkgetin derivative IP2 acts as a booster of the PTPs-derived antigenic presentation in vitro in the same way as the natural product.

The IP2 and M2P2 molecules were then tested for their anti-tumoral effect in vivo. As previously performed with isoginkgetin treatment, MCA205 sarcoma cells or B16F10 melanoma cells, stably expressing the Globin-intron-SL8 construct or WT, were subcutaneously inoculated in mice. At days 5, 10 and 15 after tumor inoculation, each group of mice were respectively intraperitoneally treated with 18 mg/kg of isoginkgetin, IP2 or M2P2. At this dose, a significant decrease of MCA205 GI tumor growth was observed after treatment with IP2 compare to isoginkgetin treatment, while no impact of M2P2 treatment was monitored (FIG. 11C, left panel). In addition, the reduction of B16F10 GI tumor growth was similar after treatment with 18 mg/kg of isoginkgetin or IP2, while M2P2 had no effect on growth (FIG. 11C, right panel). As IP2 treatment reduces tumor growth and is water soluble, inventors decided to increase the dose injected in mice. The increased dose of IP2 did not improve its anti-tumoral effect on MCA205 GI at 24 mg/kg but increased it on B16F10 GI at 36 mg/kg (FIG. 11C). Strikingly, isoginkgetin and M2P2 treatment did not impact tumor growth of either MCA205 WT or B16F10 WT, whereas IP2 treatment slows down both tumor growth (FIG. 11D). Inventors confirmed that IP2 does not induce apoptosis of tumor cells even at a high dose (FIG. 12C). Finally, IP2 treatment was shown to extend survival of mice, with more than 50% of survivors 100 days after tumor inoculation (FIG. 11E, lower panel). At the same time, around 30% of mice treated with isoginkgetin were still alive (FIG. 11E, middle panel). M2P2 treatment does not impact survival (FIG. 11E, upper panel).

Overall, these results demonstrate a correlation between an increase of PTPs-derived antigen presentation observed in vitro and a reduction of the tumor growth in vivo after treatment. Interestingly, contrary to isoginkgetin, IP2 treatment slows down the growth of tumors that do not bear the highly immunodominant SL8 epitope derived from PTPs. Inventors believe that the splicing inhibitor IP2 potentiates the apparition of immunodominant epitopes at the cell surface that drives the anti-tumoral response.

IP2 Treatment Efficacy is Dependent on the Immune-Response and Creates a Long-Lasting Anti-Tumoral Response.

To determine the requirement of the immune system and especially of the T-cell response for IP2 efficacy against tumor, inventors looked at its effect in Nu/Nu athymic nude mice that lack T-cells but not B and NK cells. As previously tested with isoginkgetin, MCA205 or B16F10 cells stably expressing the Globin-intron-SL8 construct or WT were subcutaneously inoculated in mice. At days 5, 10 and 15 after tumor inoculation, each group of mice were intraperitoneally treated with the most efficient dose of IP2 against tumor growth observed in immunocompetent mice. Hence, MCA205GI, MCA205 WT and B16F10 GI or WT bearing mice were treated with 18 mg/kg, 24 mg/kg and 36 mg/kg respectively. In each condition, no impact of IP2 treatment was observed on tumor growth (FIGS. 13A and B).

In addition, in order to assess the specific requirement of CD8$^+$ T cells for IP2 efficacy, inventors tested the impact of in vivo CD8$^+$ T cells depletion in mice. Mice were inoculated with MCA205 GI cells subcutaneously followed by a scheduled treatment with anti-CD8$^+$ T cells antibody or with the isotype 2A3. IP2 treatment was administered as previously at day 5, 10 and 15. Interestingly, anti-CD8$^+$ T cells antibody treatment completely abrogated the anti-tumoral effect of the IP2 treatment (FIG. 13C). Therefore, this result confirms that the effect of the IP2 treatment on tumor growth is dependent on the CD8$^+$ T cell response, which supports an antigen-driven cytotoxic activity against the tumor cells.

Finally, around 50% of mice inoculated with MCA205 GI and subsequently treated with IP2 as described above became tumor free after treatment. 100 days after the first tumor inoculation, these mice were re-challenged with MCA205 GI tumor cells on the right flank and with B16F10 cells on the left flank. While B16F10 tumors grew over time, MCA205 GI did not grow in mice (FIG. 13D). These results demonstrate that mice developed a long term anti-tumoral response specific to MCA205 GI tumor after IP2 treatment.

IP2 (IP2-4Na) Treatment Reduces Tumor Growth from Established Tumor

In order to assess the specific IP2 efficacy on modulating tumor growth by enhancing the proliferation of specific anti-tumor CD8$^+$ T cells, inventors tested the impact of IP2 on established tumor in vivo. MCA205 sarcoma tumor cells (15.10$^5$) stably expressing the Globin-intron-SL8 construct were injected subcutaneously and were allowed to progress 10 days before being ranked and assigned to groups of equivalent tumor burden, resulting in the formation of three groups of tumor sizes of 40, 50 and 100 mm$^2$ before initiation of IP2 treatment. Then every 3 to 4 days, each group of mice was respectively intraperitoneally treated with 24 mg/kg of IP2. At this dose, a remarkable decrease of MCA205 GI tumor growth was observed after treatment with IP2 compare to non-treated mice (FIG. 14) independently of the group tested. Even when the tumors had reached a size of 100 mm$^2$ (circle), 5 doses of 24 mg/kg of IP2 were able to induce a significant tumor regression with an increase of survival of around 30 days (grey circle) compare to the untreated mice (black circles). In conclusion, all these experiments using IP2 as immunomodulators show that this molecule is efficient to induce a complete tumor rejection when mice are treated very early (when tumor where just palpable) by inducing a long term anti-tumoral response, and show that IP2 treatment can also reduce tumor growth on established tumor.

Overall these results shed light on the capacity of specific splicing inhibitors, such as isoginkgetin and IP2, to positively modulate the anti-tumoral immune response. In addition, they confirm that PTPs-derived antigens are efficiently presented and recognized by CD8$^+$ T cells in vitro and in vivo and that a change in their presentation at the cell surface in quantity or in quality can lead to a CD8$^+$T cells response against cancer.

REFERENCES

Apcher, S. et al. Major source of antigenic peptides for the MHC class I pathway is produced during the pioneer round of mRNA translation. *Proc. Natl. Acad. Sci. U.S.A.* 108, 11572-7 (2011).

Burg, S. H. et al. Vaccines for established cancer: overcoming the challenges posed by immune evasion. *Nat. Publ. Gr.* 16, 219-233 (2016).

Caron, E. et al. The MHC I immunopeptidome conveys to the cell surface an integrative view of cellular regulation. *Mol Syst Biol.* 7, 533 (2011).

Dolan, B. P. et al. Distinct pathways generate peptides from defective ribosomal products for CD8 T cell immunosurveillance. *J. Immunol.* 186, 2065-72 (2011).

Doherty, S. J. et al. Immunoproteasome Subunit Deficiencies Impact Differentially on Two Immunodominant Influenza Virus-Specific CD8+ T Cell Responses. *J Immunol Ref* 177, 7680-7688 (2006).

Duvallet, E., et al. Exosome-driven transfer of tumor-associated Pioneer Translation Products (TA-PTPs) for the MHC class I cross-presentation pathway. *Oncoimmunology* 5, e1198865 (2016).

Kang S S, et al. Flavonoids from the leaves of Ginkgo biloba, Korea. *J Pharmacogn.* 1990; 21:111-20.

Kmieciak, M., et al. HER-2/neu antigen loss and relapse of mammary carcinoma are actively induced by T cell-mediated anti-tumor immune responses. *Eur. J. Immunol.* 37, 675-685 (2007).

Lee, S. J., et al. Suppression of mouse lymphocyte proliferation in vitro by naturally-occurring bioflavonoids. *Life Sc.* 57, 551-558 (1995).

Lee, S. & Sin, J. MC32 tumor cells acquire Ag-specific CTL resistance through the loss of CEA in a colon cancer model. *Hum Vaccin Immunother* 11, 2012-2020 (2015).

Leone, P. et al. MHC class I antigen processing and presenting machinery: organization, function, and defects in tumor cells. *J. Natl. Cancer Inst.* 105, 1172-87 (2013).

Liu, Y. et al. Expression of antigen processing and presenting molecules in brain metastasis of breast cancer. *Cancer Immunol. Immunother.* 61, 789-801 (2012).

Mellman, I., et al. Cancer immunotherapy comes of age. *Nature* 480, 480-489 (2014).

Watson, N. F. S. et al. Immunosurveillance is active in colorectal cancer as downregulation but not complete loss of MHC class I expression correlates with a poor prognosis. *Int. J. Cancer* 118, 6-10 (2006).

Yewdell, J W., et al. Defective ribosomal products (DRiPs): a major source of antigenic peptides for MHC class I molecules? *J Immunol* 157(5): 1823-6 (1996).

The invention claimed is:

1. A medicament comprising a compound of formula

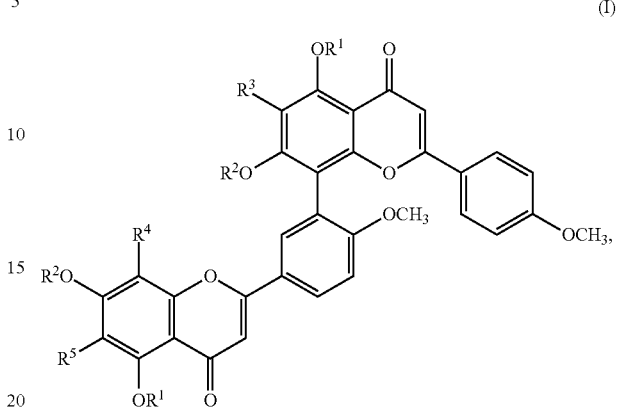

(I)

wherein $R^1$ and $R^2$ are independently selected from the group consisting of Na, H, —$CH_3$, —$CH_2$—$CH_3$, —$CH_2$—CH=$CH_3$, n-$CH_2$—$CH_2$—$CH_3$, P(O)(O—$CH_2$—$CH_3$)$_2$, P(O)(OH)$_2$ or P(O)(ONa)$_2$ and wherein $R^1$, $R^2$, $R^3$, $R^4$ and $R^5$ are not H simultaneously, wherein $R^1$ is not —$CH_3$ when $R^2$ is P(O)(ONa)$_2$ or P(O)(OH)$_2$ and each of $R^3$, $R^4$ and $R^5$ is H, and wherein $R^1$ is not —$CH_3$ or H when $R^2$ is —$CH_3$ and each of $R^3$, $R^4$ and $R^5$ is H; and wherein $R^3$, $R^4$ and $R^5$ are independently selected from the group consisting of H, $CH_3$, —$CH_2$—$CH_3$, —$CH_2$—CH=$CH_3$, and $C_nH_{2n+1}$ with n=3–10.

2. The medicament according to claim 1, wherein the compound is

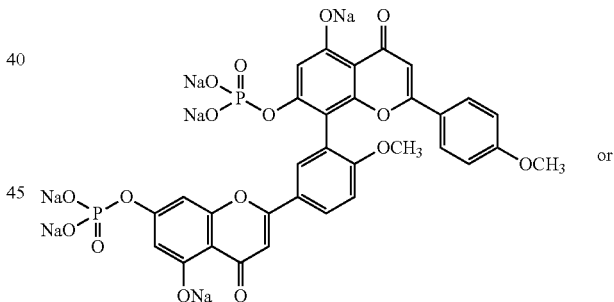

or

SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: SEQ01

<400> SEQUENCE: 1

Ser Ile Ile Asn Phe Glu Lys Leu
1               5

-continued

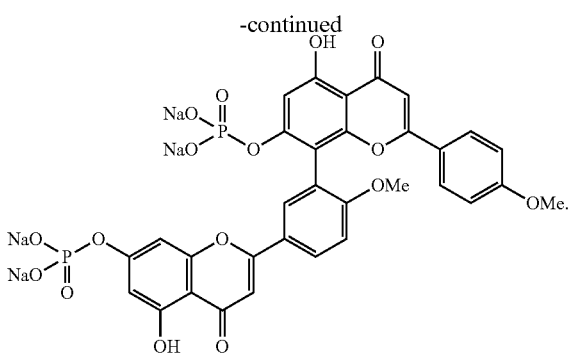

3. A method for treating melanoma, sarcoma or lung cancer in a subject in need thereof, wherein the method comprises a step of administering an effective amount of a compound according to claim 1 to the subject.

4. The method according to claim 3, wherein the compound is administered to the subject in combination with an effective amount of at least one distinct anticancer agent, and/or the method further comprises a step of exposing the subject to radiotherapy.

5. The method according to claim 3, wherein the subject has melanoma.

6. The method according to claim 3, wherein the subject has lung cancer.

7. The method according to claim 4, wherein the at least one distinct anticancer agent is selected from the group consisting of a chemotherapeutic agent, an immune checkpoint blocker and an anti-cancer vaccine.

8. The method according to claim 3, wherein the method stimulates an anti-cancer immune response in the subject.

9. The method according to claim 3, wherein the subject is a mammal.

10. The method according to claim 9, wherein the subject is a human being.

11. The method according to claim 3, wherein the compound is

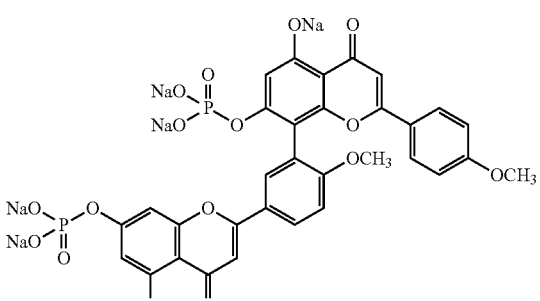

or

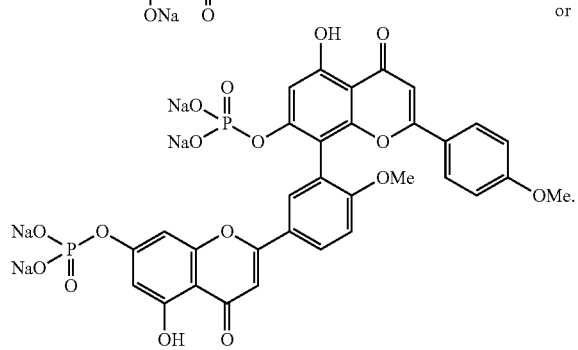

12. A composition comprising a compound of formula (I) as described in claim 1 and a pharmaceutically acceptable carrier.

13. The composition according to claim 12, wherein the composition further comprises at least one distinct anticancer agent to be used simultaneously, separately or sequentially.

14. The composition according to claim 12, wherein the compound is

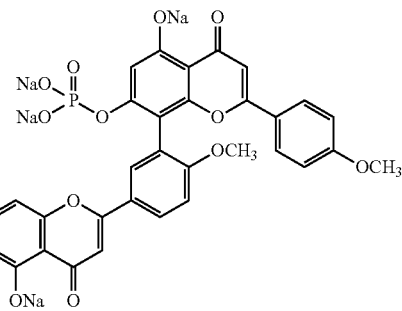

or

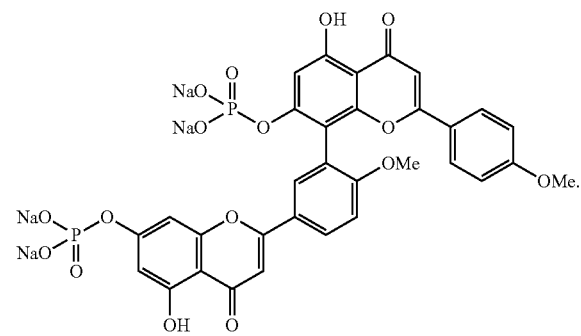

15. A method for inducing or increasing the presentation of Pioneer Translation Products (PTPs)-derived antigens by cancer cells in a subject, wherein the method comprises a step of administering the subject with an effective amount of a compound as described in claim 1.

16. The method according to claim 15, wherein the subject is a mammal.

17. The method according to claim 16, wherein the subject is a human being.

18. The method according to claim 15, wherein the compound is

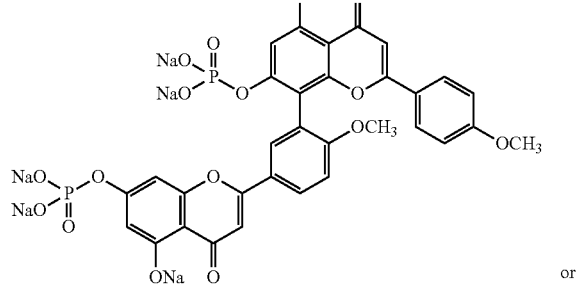

or

-continued

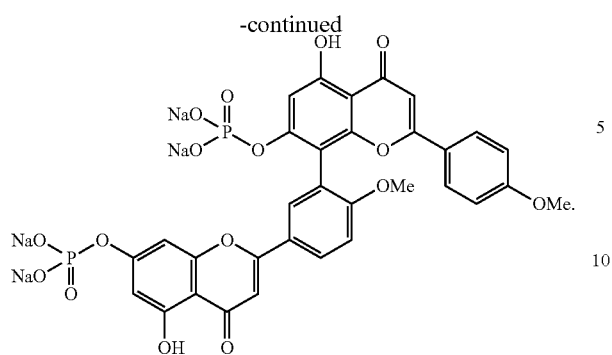

19. A kit comprising the compound of formula (I) as described in claim 1, and at least one distinct anticancer agent in distinct containers.

20. The method according to claim 3, wherein the subject has a sarcoma.

21. The method according to claim 6 wherein lung cancer is non-small cell lung cancer.

22. The method according to claim 6 wherein lung cancer is small-cell lung cancer.

* * * * *

UNITED STATES PATENT AND TRADEMARK OFFICE
CERTIFICATE OF CORRECTION

PATENT NO. : 11,110,105 B2
APPLICATION NO. : 16/604599
DATED : September 7, 2021
INVENTOR(S) : Sébastien Apcher et al.

It is certified that error appears in the above-identified patent and that said Letters Patent is hereby corrected as shown below:

In the Specification

Column 5,
Line 20, "–CH$_2$13 CH=CH$_3$," should read -- –CH$_2$–CH=CH$_3$, --.

Column 7,
Lines 36-37, "a mammal" should read --a mammal.--.

Column 10,
Line 20, "IFNa," should read --IFNα,--.

Column 13,
Line 24, "thereof Methods" should read --thereof. Methods--.

Column 29,
Line 28, "Slows Clown Tumor" should read --slows down tumor--.

Column 33,
Line 13, "CD830" should read --CD8+--.

Signed and Sealed this
Fifteenth Day of March, 2022

Drew Hirshfeld
*Performing the Functions and Duties of the*
*Under Secretary of Commerce for Intellectual Property and*
*Director of the United States Patent and Trademark Office*